(12) United States Patent
Yang et al.

(10) Patent No.: US 12,403,115 B2
(45) Date of Patent: Sep. 2, 2025

(54) ASYMMETRIC SYNTHESIS AND USES OF COMPOUNDS IN DISEASE TREATMENTS

(71) Applicant: Zhejiang Jiachi Development Pharmaceuticals LTD., Hangzhou (CN)

(72) Inventors: Jun Yang, Hangzhou (CN); Wenping Xu, Hangzhou (CN)

(73) Assignee: Zhejiang Jiachi Development Pharmaceuticals LTD, Hangzhou (CN)

( * ) Notice: Subject to any disclaimer, the term of this patent is extended or adjusted under 35 U.S.C. 154(b) by 348 days.

(21) Appl. No.: 16/641,145

(22) PCT Filed: Aug. 22, 2018

(86) PCT No.: PCT/CN2018/101629
§ 371 (c)(1),
(2) Date: Feb. 21, 2020

(87) PCT Pub. No.: WO2019/042192
PCT Pub. Date: Mar. 7, 2019

(65) Prior Publication Data
US 2020/0179323 A1    Jun. 11, 2020

(30) Foreign Application Priority Data
Aug. 28, 2017  (WO) ................ PCT/CN2017/099221

(51) Int. Cl.
| C07J 75/00 | (2006.01) |
| A61K 31/138 | (2006.01) |
| A61K 31/22 | (2006.01) |
| A61K 31/4196 | (2006.01) |
| A61K 31/56 | (2006.01) |
| A61K 45/06 | (2006.01) |
| C07J 61/00 | (2006.01) |

(52) U.S. Cl.
CPC ............ *A61K 31/22* (2013.01); *A61K 31/138* (2013.01); *A61K 31/4196* (2013.01); *A61K 45/06* (2013.01)

(58) Field of Classification Search
CPC .......... A61K 31/56; C07J 61/00; C07J 75/005
See application file for complete search history.

(56) References Cited

U.S. PATENT DOCUMENTS

| 4,522,831 A | 6/1985 | Chatterton, Jr. |
| 5,001,120 A | 3/1991 | Li |
| 2003/0027803 A1 | 2/2003 | Slaga et al. |
| 2006/0270845 A1 | 11/2006 | Kuenzer et al. |
| 2010/0227841 A1 | 9/2010 | Stickney et al. |
| 2016/0045516 A1 | 2/2016 | White et al. |
| 2017/0151263 A1* | 6/2017 | Yang ....................... A61K 45/06 |

FOREIGN PATENT DOCUMENTS

| CN | 1331082 A | 1/2002 |
| CN | 102218069 A | 10/2011 |
| CN | 104208069 A | 12/2014 |
| FR | 2438055 A1 | 4/1990 |
| WO | 200047603 A2 | 8/2000 |
| WO | 200047603 A3 | 8/2001 |
| WO | 2005097141 A2 | 10/2005 |
| WO | 2005097141 A3 | 3/2006 |
| WO | 2006081152 A2 | 8/2006 |
| WO | 2006081152 A3 | 2/2007 |
| WO | 2009149392 A1 | 12/2009 |
| WO | 2010060215 A1 | 6/2010 |
| WO | 2012083090 A2 | 6/2012 |
| WO | 2012083090 A3 | 12/2012 |
| WO | 2015169173 A1 | 11/2015 |

OTHER PUBLICATIONS

Hildebrandt et al. J. Org. Chem. 2006, 71, 6728-6733.*
Alexanderson, P. et al. (2001). "Ipriflavone in the Treatment of Postmenopausal Osteoporosis A Randomized Controlled Trial," JAMA. 285(11):1482-1488.
Banik, U.K. et al. (Dec. 1962). "Effect of Steroidal Anti-Progestins on Implantation of Fertilized Eggs of Rats and Mice," Proc. Soc. Expt. Biol. Med. 111(3):595-597.
Barrett-Connor, E. et al. (Jul. 13, 2006). "Effects of Raloxifene on Cardiovascular Events and Breast Cancer in Postmenopausal Women," N Engl. J. Med. 355 (2):125-137.
Boonyaratanakornkit, V. (2011). "Scaffolding Proteins Mediating Membrane-Initiated Extra-Nuclear Actions of Estrogen Receptor," Steroids 76(9): 877-884.
Gu, W. et al. (Mar. 7, 2017). "Anordrin Eliminates Tamoxifen Side Effects without Changing Its Antitumor Activity," Sci Rep. 7:43940, 9 pages.
Hershberger, P.A. et al. (Aug. 2009 e-pub May 19, 2009). "Estrogen Receptor Beta (ErB) Subtype-Specific Ligands Increase Transcription, p44/p42 Mitogen Activated Protein Kinase (MAPK) Activation and Growth in Human Non-Small Cell Lung Cancer Cells 1," J. of Steroid Biochem. & Mol. Biol. 116(1-2):102-109.
International Preliminary Report on Patentability, issued Mar. 3, 2020, for PCT Application No. PCT/CN2017/099221, 7 pages.
International Search Report and Written Opinion, dated May 25, 2018, for PCT Application No. PCT/CN2017/099221, 10 pages.

(Continued)

*Primary Examiner* — Irina Neagu
(74) *Attorney, Agent, or Firm* — MORRISON & FOERSTER LLP

(57) ABSTRACT

The present application discloses, among other things, asymmetric synthesis a diastereomeric compound of formula (I) (e.g., α-anordrin) or salt thereof. Also provided are methods and compositions for treatment of estrogen deficiency as well as preventing or reducing an estrogen deficiency symptom using a diastereomeric compound of formula (I) (e.g., α-anordrin) or salt thereof alone or in combination with at least one additional agent. Further provided are methods and compositions for reducing a side effect of an additional agent in the context of combination therapy with a diastereomeric compound of formula (I) (e.g., α-anordrin) or salt thereof.

22 Claims, 12 Drawing Sheets

(56) References Cited

OTHER PUBLICATIONS

Kuang, L. et al. (Apr. 2010). "Involvement of Estrogen Receptor Variant ER-a36, Not GPR30, in Nongenomic Estrogen Signaling," Molecular endocrinology. 24(4):709-721.

Li, Z-H. et al. (Dec. 1990). "X-Ray Diffraction Studies on the Absolute Configuration of α- and β-anordrins," Steroids 55(12):565-570.

Ma, Z.C. et al. (Oct. 2000). "Antiangiogenic Effect of Alpha-Anordrin In Vitro and In Vivo," Acta Pharmacol. Sin 21 (10):939-944.

Mauvais-Jarvis, F. et al. (Jun. 2013). "The Role of Estrogens in Control of Energy Balance and Glucose Homeostasis," Endocrine Reviews 34(3):309-338.

Mehta, R.R. et al. (Dec. 1981). "Antiestrogenic and Antifertility Actions of Anordrin, (2α, 17α-diethynyl-A-nor-5α-androstane-2β, 17β-diol 2,17-dipropionate)," Steroids 38(6):679-691.

Minssen, M et al. (Jan. 1, 1995). "N° 13. —Dérivés du A-no (5a) androstane. 1. —Alcools Acétyléniques et chloracétylénique en positions 2," Bulletin De La Societe Chimique De France, Society Francaise De Chime, Paris, France, pp. 71-76. English Abstract.

Nehra, R et al. (Jun. 2010). "BCL2 And CASP8 Regulation by NF-KB Differentially Affect Mitochondrial Function and Cell Fate in Antiestrogen-Sensitive and -Resistant Breast Cancer Cells," FASEB J. 24(6):2040-2055.

Nilsson, B.O. et al. (Jul. 2011). "G Protein-Coupled Oestrogen Receptor 1(GPER1)/GPR30: A New Player in Cardiovascular and Metabolic Oestrogenic Signaling," British Journal of Pharmacology. 163(6):1131-1139.

O'Brien, J.E. et al. (Jul. 17, 2006) "Estrogen Induced Proliferation of Uterine Epithelial Cells Is Independent of Estrogen Receptor a Binding to Classical Estrogen Response Elements," J. of Biol. Chem. 281(36):26683-26692.

Perreault, M. et al. (2016, e-pub. Aug. 21, 2016). "Explorative Study on the Anticancer Activity, Selectivity and Metabolic Stability of Related Analogs of Aminosteroid RM-133," Steroids 115:105-113.

Pincus, G. et al. (1965). "Steroidal Inhibitors of a Cell-Division-Inducing System In Vitro," Steroids 58(SUPPL 1):193-197.

Rao, J. et al. (2011). "Advances in the Understanding of the Structure and Function of ER-A36, a Novel Variant of Human Estrogen Receptor-Alpha," Journal of Steroid Biochemistry and Molecular Biology. 127(Issues 3-5):231-237.

Revankar, C.M. et al. (Mar. 11, 2005). "A Transmembrane Intracellular Estrogen Receptor Mediates Rapid Cell Signaling," Science 307 (Issue 5715):1625-1630.

Supplementary Partial European Search Report, dated Apr. 8, 2021, for European Patent Application No. 18852205.6, 13 pages.

Takamura, T. et al. (2007 e-pub May 1, 2007). "Selective Estrogen Receptor Modulator Raloxifene-Associated Aggravation of Nonalcoholic Steatohepatitis," Internal Med. 46(9):579-581.

Xu, P. et al. (1989). "Antitumor Action of Anordrin on Experimental Tumors," Tumor 9:197-199, English Abstract, 3 pages.

Yoshida, M. et al. (Apr. 26, 2007, e-pub. Mar. 28, 2007). "Palladium-Catalyzed Diastereoselective Coupling of Propargylic Oxiranes With Terminal Alkynes," Organic Letters 9(9):1643-1646 with Supporting Information, 75 pages.

Zhang, X.T. et al. (Jan. 2012). "Estrogen Receptor-α 36 Mediates Mitogenic Antiestrogen Signaling in ER-Negative Breast Cancer Cells," PLos one. 7(1):e30174, 12 pages.

Chatterton, R.T. et al. (Mar. 1, 1989). "Anti-Uterotrophic and Folliculostatic Activities of Anordiol (2α, 17α- diethynyl-A-nor-5α-androstane-2β, 17β-diol)," Contraception 39(3):291-297.

Crabbe, P. et al. (Jan. 1, 1978). "Chemical Synthesis and Bioassay of Anordrin and Dinordrin I and II." Steroids 33(1):85-96.

Vincze, I. et al. (May 1, 1993). "Developing a Radioimmunoassay for Anordrin: The Synthesis of Propionyl and Hemisuccinyl Esters of Anordiol," Contraception 47(5):507-514.

Extended European Search Report, dated Jul. 16, 2021, for European Patent Application No. 18852205.6, 18 pages.

* cited by examiner

ASYMMETRIC SYNTHESIS AND USES OF COMPOUNDS IN DISEASE TREATMENTS

CROSS REFERENCE TO RELATED APPLICATIONS

This application is the U.S. national phase application under 35 U.S.C. § 371 of International Application No. PCT/CN2018/101629, filed on Aug. 22, 2018, which claims priority to International Application No. PCT/CN2017/099221, filed on Aug. 28, 2017.

TECHNICAL FIELD

The present invention pertains to the field of asymmetric synthesis of a steroid-like compound, and more particularly, to a method for preparing a chiral compound of anordrin and analog thereof. This invention also relates to therapeutic use of a chiral compound in replacing treatment of estrogen-deficiency symptoms.

BACKGROUND

The decreased production of estrogen in ovariectomized (OVX) or postmenopausal or anti-estrogen therapy women leads to estrogen-deficiency symptoms that may adversely affect their quality of life for decades. Estrogen replacement therapy (ERT) has been utilized to treat these symptoms since the 1940s.

Estrogen binds to its receptors to regulate RNA transcription, stimulate cell proliferation and modulate metabolic signaling in many tissues during mammalian reproduction and development. Three genes for estrogenic binding proteins have been identified, encoding estrogen receptor (ER) a and 3, and G-protein coupled estrogen receptor 1 (GPER1). ER-α and β have similar structural and functional domains, containing activation function domain 1 (AF-1), a DNA binding domain (DBD), a dimerization domain and activation function domain 2 (AF-2), which is the ligand binding domain (LBD). They both belong to the nuclear super family of ligand-dependent transcription factors and have highly conserved DBD and LBD regions. They regulate RNA transcription upon ligand binding, which results in ligand-receptor complexes that can dimerize and translocate into the nucleus, where they bind to estrogen response elements (EREs) found in the promoters of estrogen-responsive genes. This type of modulation is typically referred to as the classical estrogen pathway. ER-α and β also regulate diverse biological functions through membrane-initiated estrogen signaling (MIES), associating with plasma membrane by interaction with their ligand binding domain. The detailed molecular mechanisms of signaling by membrane-associated ERs are still unclear. The modulatory effects of estrogen mediated by membrane-associated receptors on cell proliferation, matrix/migration, metabolism and glucose homeostasis have been reviewed (1, 2). Furthermore, studies on ER knockout mice indicate that ER-α is the dominant functional estrogen receptor, as compared to ER-β. Three transcription variants of ER-α, 66, 46 and 36, have been found. ER-α36 lacks the AF-1 domain and contains a partial ligand binding domain. It has been found localized to the cell membrane and cytosol. Since ER-α-36 is restricted to modulating MIES and was found to be uniquely expressed in tamoxifen-resisted cancer cells, such as MDA-MB-231 and HecIA, MIES modulated by membrane-associated ER is thought to be responsible for the resistance to anti-estrogen therapy found by some researchers (3, 4).

However, studies showing an increased risk of breast and uterine cancer, as well as thromboembolism morbidity, associated with ERT have led to a decline in its usage. Combined administration of estrogen and progesterone prevents the risk of breast and uterine cancers, but it causes progesteron side effects such as dizziness, nausea, vomiting, fatigue, anxiety, depression and headache etc. The postmenopausal symptoms remain a problem for many older women. Therefore, there remains a continuing need for new development of replacing treatment of estrogen-deficiency symptoms.

BRIEF SUMMARY OF THE INVENTION

The present application in one aspect provides a method of synthesizing a diastereomeric compound of formula (I) (such as α-anordrin) or salt thereof. In accordance with various embodiments described herein, a diastereomeric compound of formula (I) (such as α-anordrin) or salt thereof is substantially pure.

In another aspect, there is provided a method of treating estrogen deficiency or preventing or reducing estrogen-deficiency symptoms including an OVX or postmenopausal symptom, in an individual, comprising administering to the individual: a) an effective amount of a diastereomeric compound of formula (I) (such as α-anordrin) or salt thereof; and optionally b) an effective amount of at least one additional agent selected from the group consisting of a selective estrogen receptor modulator and an aromatase inhibitor. In some embodiments, the additional agent is a selective estrogen receptor modulator (SERM) selected from the group consisting of tamoxifen, raloxifene, lasofoxifene, bazedoxifene, arzoxifene, ormeloxifene, ospemifene, and levormeloxifene. In some embodiments, the additional agent is an aromatase inhibitor selected from the group consisting of anastrozole, letrozole, exemestane, vorozole, formestane, and fadrozole. In some embodiments, the estrogen-deficiency symptom is selected from the group consisting of high liver triglyceride, osteoporosis, vulvovagina atrophy, high blood triglyceride, high blood glucose and weight gain.

In some embodiments, there is provided a method of reducing a side effect of at least one additional agent by a diastereomeric compound of formula (I) (such as α-anordrin) or salt thereof, comprising administering to the individual an effective amount of a diastereomeric compound of formula (I) (such as α-anordrin) or salt thereof in combination with the additional agent, wherein the additional agent is selected from the group consisting of a selective estrogen receptor modulator and an aromatase inhibitor. In some embodiments, the additional agent is tamoxifen. In some embodiments, the additional agent is a selective estrogen receptor modulator (SERM) selected from the group consisting of tamoxifen, raloxifene, lasofoxifene, bazedoxifene, arzoxifene, ormeloxifene, ospemifene, and levormeloxifene. In some embodiments, the additional agent is an aromatase inhibitor selected from the group consisting of anastrozole, letrozole, exemestane, vorozole, formestane, and fadrozole.

In some embodiments, a diastereomeric compound of formula (I) or salt thereof and the additional agent are administered sequentially. In some embodiments, a diastereomeric compound of formula (I) or salt thereof and the additional agent are administered simultaneously.

In some embodiments, the individual is human.

In yet another aspect, there is provided a pharmaceutical composition comprising a diastereomeric compound of formula (I) (such as α-anordrin) or salt thereof and at least one additional agent selected from the group consisting of a selective estrogen receptor modulator (SERM) and an aromatase inhibitor. In some embodiments, the additional agent is tamoxifen. In some embodiments, the additional agent is raloxifene or functional equivalent thereof (including for example raloxifene, lasofoxifene, or bazedoxifene). In some embodiments, the additional agent is an aromatase inhibitor, such as anastrozole or functional equivalent thereof.

In some embodiments, the weight ratio of a diastereomeric compound of formula (I) (such as α-anordrin) or salt thereof and the additional agent in the composition is about 1:20 to about 20:1 (including for example about 10:1 to about 1:10, or about 1:10 to about 1:15).

A pharmaceutical composition according to the present invention can be present in a unit dosage form, for example an oral unit dosage form, such as capsules, tablets, pills, caplets, gels, liquids (e.g., suspensions, solutions, emulsions), powders or other particulates, and so forth.

Also provided are methods of using a pharmaceutical composition described herein for treating estrogen deficiency, or preventing or reducing estrogen-deficiency symptoms including an OVX or postmenopausal symptom as described herein.

These and other aspects and advantages of the present invention will become apparent from the subsequent detailed description and the appended claims. It is to be understood that one, some, or all of the properties of the various embodiments described herein may be combined to form other embodiments of the present invention.

BRIEF DESCRIPTION OF FIGURES

FIG. 1: The separation of α-anordrin and β-anordrin using silica gel.

FIG. 3: Lower dosage of α-anordrin (α-ANO) did not prevent the uterus atrophy of OVX female mice compared with sham group.

FIG. 4: The α-anordrin (α-ANO) shows dosage dependent activity to prevent the atrophy of vulvovagina compared with β-anordrin (β-ANO) in OVX female mice.

FIG. 5: The α-anordrin shows dosage dependent activity to decrease the amount of blood glucose, TG and body mass compared with β-anordrin in OVX female mice.

(FIG. 6A) Paraffin-embedded H&E sections (10× magnifications) of mice liver treated by drugs for four weeks. (FIG. 6B) Statistically analyzing the amount of TG in mice liver (mg/g), as measured from H&E-stained sections, as in (FIG. 6A). N=12.

FIG. 7: The micro-CT result shows that α-anordrin is more actively to prevent the osteoporosis compared with β-anordrin in OVX female mice.

FIG. 8: The α-anordrin inhibits tamoxifen-induced uterine EEC mitosis. TAM or a-ANO or b-ANO: mice were treated with tamoxifen (TAM) or α-anordrin (α-ANO) or β-anordrin (b-ANO) alone. TAM+α-ANO or TAM+b-ANO mice were treated with the combination of tamoxifen and α-anordrin or β-anordrin, respectively. Blank mice were treated by vehicle.

(FIG. 9A) Paraffin-embedded H&E sections (40× magnifications) of normal mouse liver treated by drugs. (FIG. 9B) Statistical analysis of liver triglyceride (TG) content, as in (A); N=6; * and ** mean P<0.05 and P<0.01, respectively.

FIG. 10: The micro-CT result shows that α-anordrin inhibits anastrozole-induced osteoporosis in bone. ANA: mice were treated with anastrozole (ANA) alone. ANA+α-ANO or ANA+b-ANO: mice were treated with the combination of anastrozole with equal amount of α-anordrin or β-anordrin, respectively. Blank mice were treated by vehicle.

FIG. 11: The α-anordrin inhibits anastrozole-induced vagina atrophy. ANA: mice were treated with anastrozole (ANA) alone. ANA+α-ANO or ANA+b-ANO: mice were treated with the combination of anastrozole with equal amount of α-anordrin or β-anordrin, respectively. Blank mice were treated by vehicle.

DETAILED DESCRIPTION OF THE INVENTION

Figure 1A:
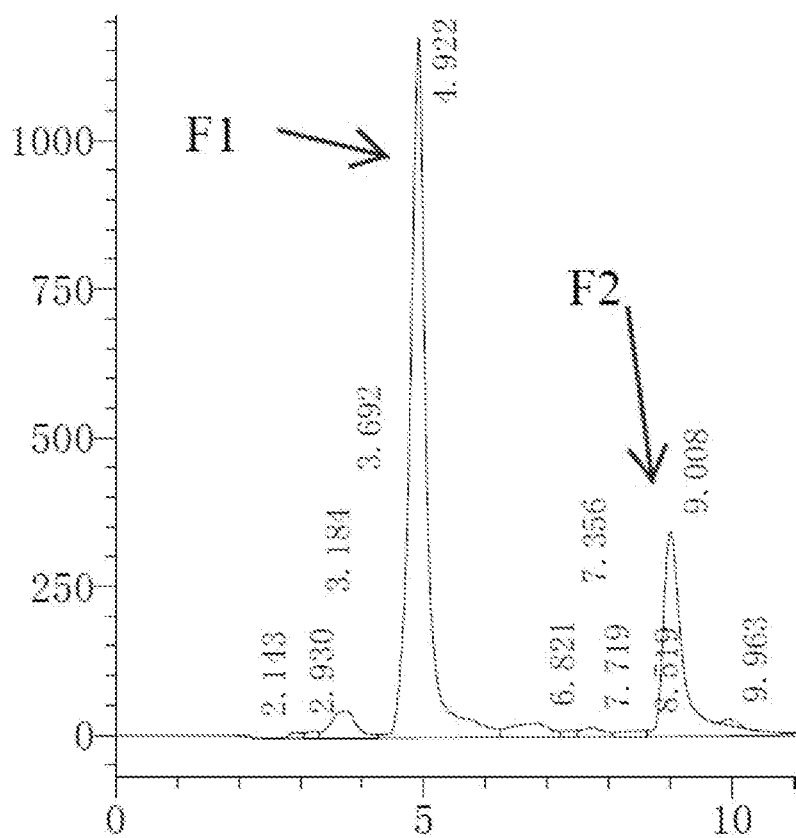
(FIG. 1A) The separation of α-anordrin (fraction 1 (F1)) and β-anordrin (fraction 2 (F2)) from the product of synthesis method I.

The present application provides methods of synthesizing a diastereomeric compound of formula (I) (such as α-anordrin) or salt thereof. Also provided are using a diastereomeric compound of formula (I) (such as α-anordrin) or salt thereof in treating estrogen deficiency or preventing or reducing estrogen-deficiency symptoms including OVX or postmenopausal symptoms in an individual. Additionally, compositions are provided for combination therapy comprising administering a diastereomeric compound of formula (I) (such as α-anordrin) or salt thereof in conjunction with an additional agent for treatment of estrogen deficiency, reducing a side effect or preventing or reducing estrogen-deficiency symptoms including OVX or postmenopausal symptoms including an OVX or postmenopausal symptom, such as high liver triglyceride, osteoporosis, vulvovagina atrophy, high blood triglyceride, high blood glucose and weight gain.

The inventions are based on the discovery of the unique properties and mechanism of actions of a diastereomeric compound of formula (I) (such as α-anordrin) or salt thereof. It was recognized in the present application that a diastereomeric compound of formula (I) (such as α-anordrin) or salt thereof is a more active selective estrogen receptor modulator of membrane-associated estrogen binding proteins compared with other diastereomeric compound of formula (I) (such as β-anordrin). The beneficial effects of a diastereomeric compound of formula (I) (such as α-anordrin) or salt thereof may include: i) the modulation of estrogen metabolic effect as an agonist which leads to prevention or reduction of estrogen-deficiency symptoms including OVX or postmenopausal symptoms, such as high liver triglyceride, osteoporosis, vulvovagina atrophy, high blood triglyceride, high blood glucose and weight gain, ii) the neutralization of detrimental effects by drugs such as tamoxifen and anastrozole, which include, for example, osteoporosis, non-alcohol steatohepatitis (NASH), atrophy of organs and endometrium cancer.

Definitions

As a person of ordinary skill in the art would appreciate, in stereochemistry, each of two or more compounds differing only in the spatial arrangement of their atoms is regarded as a diastereomer.

A compound or a salt thereof prepared by a method according to the present application may in one aspect be substantially pure diastereomeric. Compositions comprising a compound as detailed herein or a salt thereof are provided, such as a composition comprising a substantially pure diastereomeric compound. "Substantially pure diastereomeric" intends a compound that contains an insignificant amount of impurity, wherein the impurity denotes diastereomers other than a specific diastereomeric compound. In some embodiments, a substantially pure diastereomeric compound or a salt thereof is provided wherein the percentage of a diasteromer or a salt thereof is no less than about 98%. In accordance with the present application, the percentage may be no less than about 99%, about 99.5% or about 99.9%.

It is to be understood by a person of ordinary skill in the art that the combination therapy methods described herein requires that one agent or composition be administered in conjunction with an additional agent. "In conjunction with" refers to administration of one treatment modality in addition to another treatment modality, such as administration of a diastereomeric compound of formula (I) (such as α-anordrin) or salt thereof in addition to administration of the second agent to the same individual. As such, "in conjunction with" refers to administration of one treatment modality before, during or after delivery of the other treatment modality to the individual.

The methods described herein are generally useful for treatment of diseases. As used herein, "treatment" is an approach for obtaining beneficial or desired clinical results. Also encompassed by "treatment" is a reduction of pathological consequence of a proliferative disease. The methods of the invention contemplate any one or more of these aspects of treatment.

The term "effective amount" used herein refers to an amount of a compound or composition sufficient to treat a specified disorder, condition or disease such as ameliorate, palliate, lessen, and/or delay one or more of its symptoms. In reference to cancers, an effective amount comprises an amount sufficient to cause a tumor to shrink and/or to decrease the growth rate of the tumor (such as to suppress tumor growth) or to prevent or delay other unwanted cell proliferation.

The term "individual" is a mammal, including humans. An individual includes, but is not limited to, human, bovine, horse, feline, canine, rodent, or primate. In some embodiments, the individual is human. In some embodiments, the individual is an animal.

As used in this application, "alkyl" refers to a linear or branched saturated hydrocarbon. In some embodiments, alkyl groups are those having 1 to 20 carbon atoms (a "$C_1$-$C_{20}$ alkyl"). In some embodiments, an alkyl group has 1 to 12 carbon atoms (i.e., ($C_1$-$C_{12}$alkyl)), or 1 to 10 carbon atoms (i.e., ($C_1$-$C_{10}$alkyl)), or 1 to 8 carbon atoms (i.e., ($C_1$-$C_8$alkyl)), or 1 to 6 carbon atoms (i.e., ($C_1$-$C_6$alkyl)), or 1 to 4 carbon atoms (i.e., ($C_1$-$C_4$alkyl)). Examples of suitable alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), and octyl (—$(CH_2)_7CH_3$).

"-Alkyl-" refers to a bivalent radical derived from alkyl as described above. In some embodiments, -alkyl- as used herein has at least 1 carbon atom, at least 2 carbon atoms, at least 3 carbon atoms, at least 4 carbon atoms, at least 5 carbon atoms, at least 6 carbon atoms, at least 10 carbon atoms; at least 12 carbon atoms; at least 20 carbon atoms; or at least 40 carbon atoms; or 1 to 40 carbon atoms, 1 to 30 carbon atoms, 1 to 25 carbon atoms, 1 to 20 carbon atoms, 5 to 20 carbon atoms, 12 to 20 carbon atoms, or 14 to 18 carbon atoms. Examples of -alkyl- include, but are not limited to, groups such as methylene (—CH$_2$—), ethylene (—CH$_2$CH$_2$—), propylene (—CH$_2$CH$_2$CH$_2$—), butylene (—CH$_2$CH$_2$CH$_2$CH$_2$—), and the like.

"Alkenyl" as used herein refers to a linear or branched hydrocarbon with at least one carbon-carbon double bond. In some embodiments, an alkenyl group has 2 to 12 carbon atoms (i.e., $C_2$-$C_{12}$alkenyl), or 2 to 10 carbon atoms (i.e., $C_2$-$C_{10}$alkenyl), or 2 to 8 carbon atoms (i.e., $C_2$-$C_8$alkenyl), or 2 to 6 carbon atoms (i.e., $C_2$-$C_6$alkenyl), or 2 to 4 carbon atoms (i.e., $C_2$-$C_4$alkenyl). Examples of suitable alkenyl groups include, but are not limited to, ethylene or vinyl (—CH═CH$_2$), allyl (—CH$_2$CH═CH$_2$) and 5-hexenyl (—CH$_2$CH$_2$CH$_2$CH$_2$CH═CH$_2$).

"-Alkenyl-" refers to a bivalent radical derived from alkenyl as described above. In some embodiments, -alkenyl- as used herein has at least 2 carbon atoms, at least 3 carbon atoms, at least 4 carbon atoms, at least 5 carbon atoms, at least 6 carbon atoms, at least 10 carbon atoms; at least 12 carbon atoms; at least 20 carbon atoms; or at least 40 carbon atoms; or 1 to 40 carbon atoms, 1 to 30 carbon atoms, 1 to 25 carbon atoms, 1 to 20 carbon atoms, 5 to 20 carbon atoms, 12 to 20 carbon atoms, or 14 to 18 carbon atoms. To give an example, -alkenyl- may be —CH═CH—.

"Alkynyl" as used herein refers to an unsaturated linear or branched univalent hydrocarbon chain or combination thereof, having at least one site of acetylenic unsaturation (i.e., having at least one moiety of the formula C—C). Alkynyl groups can have the number of carbon atoms designated (i.e., $C_2$-$C_{20}$ means 2 to 20 carbon atoms). In some embodiments, alkynyl groups are those having 2 to 12 carbon atoms (i.e., "$C_2$-$C_{12}$ alkynyl"), having 2 to 10 carbon atoms (i.e., "$C_2$-$C_{10}$ alkynyl"), having 2 to 8 carbon atoms (i.e., "$C_2$-$C_8$ alkynyl"), having 2 to 6 carbon atoms (i.e., "$C_2$-$C_6$ alkynyl"), or having 2 to 4 carbon atoms (i.e., "$C_2$-$C_4$ alkynyl"). Examples of alkynyl include, but are not limited to, groups such as ethynyl (or acetylenyl), prop-1-ynyl, prop-2-ynyl (or propargyl), but-1-ynyl, but-2-ynyl, but-3-ynyl, homologs and isomers thereof, and the like.

The term "aryl" refers to and includes polyunsaturated aromatic hydrocarbon groups. Aryl may contain additional fused rings (e.g., from 1 to 3 rings), including additionally fused aryl, heteroaryl, cycloalkyl, and/or heterocyclyl rings. In one variation, the aryl group contains from 6 to 14 annular carbon atoms. Examples of aryl groups include, but are not limited to, phenyl, naphthyl, biphenyl, and the like.

The term "cycloalkyl" refers to and includes cyclic univalent hydrocarbon structures, which may be fully saturated, mono- or polyunsaturated, but which are non-aromatic, having the number of carbon atoms designated (e.g., $C_1$-$C_{10}$ means one to ten carbons). Cycloalkyl can consist of one ring, such as cyclohexyl, or multiple rings, such as adamantly, but excludes aryl groups. A cycloalkyl comprising more than one ring may be fused, spiro or bridged, or combinations thereof. A preferred cycloalkyl is a cyclic hydrocarbon having from 3 to 13 annular carbon atoms. A more preferred cycloalkyl is a cyclic hydrocarbon having from 3 to 8 annular carbon atoms (a "$C_3$-$C_8$ cycloalkyl"). Examples of cycloalkyl include, but are not limited to, cyclopropyl, cyclobutyl, cyclopentyl, cyclohexyl, 1-cyclohexenyl, 3-cyclohexenyl, cycloheptyl, norbornyl, and the like.

"Halo" or "halogen" refers to elements of the Group 17 series having atomic number 9 to 85. Preferred halo groups include fluoro, chloro, bromo and iodo. Where a residue is substituted with more than one halogen, it may be referred to by using a prefix corresponding to the number of halogen moieties attached, e.g., dihaloaryl, dihaloalkyl, trihaloaryl etc. refer to aryl and alkyl substituted with two ("di") or three ("tri") halo groups, which may be but are not necessarily the same halo; thus 4-chloro-3-fluorophenyl is within the scope of dihaloaryl. An alkyl group in which each hydrogen is replaced with a halo group is referred to as a "perhaloalkyl." A preferred perhaloalkyl group is trifluoroalkyl (—CF$_3$). Similarly, "perhaloalkoxy" refers to an alkoxy group in which a halogen takes the place of each H in the hydrocarbon making up the alkyl moiety of the alkoxy group. An example of a perhaloalkoxy group is trifluoromethoxy (—OCF$_3$).

The term "heteroaryl" refers to and includes unsaturated aromatic cyclic groups having from 1 to 10 annular carbon atoms and at least one annular heteroatom, including but not limited to heteroatoms such as nitrogen, oxygen and sulfur, wherein the nitrogen and sulfur atoms are optionally oxidized, and the nitrogen atom(s) are optionally quaternized. A heteroaryl group can be attached to the remainder of the molecule at an annular carbon or at an annular heteroatom. Heteroaryl may contain additional fused rings (e.g., from 1 to 3 rings), including additionally fused aryl, heteroaryl, cycloalkyl, and/or heterocyclyl rings. Examples of heteroaryl groups include, but are not limited to, pyridyl, pyrimidyl, thiophenyl, furanyl, thiazolyl, and the like.

The term "heterocycle" or "heterocyclyl" refers to a saturated or an unsaturated non-aromatic group having from 1 to 10 annular carbon atoms and from 1 to 4 annular heteroatoms, such as nitrogen, sulfur or oxygen, and the like, wherein the nitrogen and sulfur atoms are optionally oxidized, and the nitrogen atom(s) are optionally quaternized. A heterocyclyl group may have a single ring or multiple condensed rings, but excludes heteroaryl groups. A heterocycle comprising more than one ring may be fused, spiro or bridged, or any combination thereof. In fused ring systems, one or more of the fused rings can be aryl or heteroaryl. Examples of heterocyclyl groups include, but are not limited to, tetrahydropyranyl, dihydropyranyl, piperidinyl, piperazinyl, pyrrolidinyl, thiazolinyl, thiazolidinyl, tetrahydrofuranyl, tetrahydrothiophenyl, 2,3-dihydrobenzo[b]thiophen-2-yl, 4-amino-2-oxopyrimidin-1 (2H)-yl, and the like.

"Optionally substituted" unless otherwise specified means that a group may be unsubstituted or substituted by one or more (e.g., 1, 2, 3, 4 or 5) of the substituents listed for that group in which the substituents may be the same of different. In one embodiment, an optionally substituted group has one substituent. In another embodiment, an optionally substituted group has two substituents. In another embodiment, an optionally substituted group has three substituents. In another embodiment, an optionally substituted group has four substituents. In some embodiments, an optionally substituted group has 1 to 2, 2 to 5, 3 to 5, 2 to 3, 2 to 4, 3 to 4, 1 to 3, 1 to 4 or 1 to 5 substituents.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

It is understood that aspect and embodiments of the invention described herein include "consisting" and/or "consisting essentially of" aspects and embodiments.

Reference to "about" a value or parameter herein includes (and describes) variations that are directed to that value or parameter per se. For example, description referring to "about X" includes description of "X".

As used herein and in the appended claims, the singular forms "a", "or" and "the" include plural referents unless the context clearly dictates otherwise.

Compounds and Synthesis

The present disclosure includes a specific stereochemical form of compounds described. In stereochemistry, each of two or more compounds differing only in the spatial arrangement of their atoms is regarded as a diastereomer. A diastereomeric compound as detailed herein may be substantially pure.

Generally speaking, chromatography, recrystallization and other conventional separation procedures may be used with intermediates or final products to obtain a particular isomer of a compound. In some embodiments, a diastereomeric compound as detailed herein can be prepared by a resolution where the diasteromeric compound is separated from a mixture of diasteromers. In other embodiments, a diastereomeric compound is prepared via asymmetric synthesis where a substantially pure diastereomeric compound or salt thereof is obtained.

In some aspects, the present disclosure describes asymmetic synthesis that results in a substantially pure diastereomeric compound or salt thereof. Provided herein are methods of preparing a substantially pure diastereomer form of a compound or a salt thereof.

According to the present invention, compounds are steroid-like compounds as detailed herein. For example, anordrin is a steroid-like estrogen. In some embodiments, a diastereomeric compound is α-anordrin, (2α, 17α)-diethynyl-(2β, 17β)-diol-dipropionate-A-nor-5α-androstane).

In some embodiments, a diastereomeric compound has the structure of Formula (I):

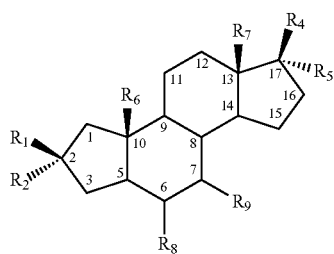

(I)

or a salt thereof, wherein
$R_1$ is —OH, —OC(O)—$R^{1a}$ or, —OC(O)$R^{1b}$COOH and $R_4$ is —OH, —OC(O)—$R^{4a}$ or, —OC(O)$R^{4b}$COOH, wherein $R^{1a}$ and $R^{4a}$ are independently hydrogen, $C_1$-$C_6$alkyl, $C_2$-$C_6$alkenyl, $C_2$-$C_6$ alkynyl or $C_3$-$C_6$ cycloalkyl, and $R^{1b}$ and $R^{4b}$ are independently —$C_1$-$C_6$alkyl- or —$C_2$-$C_6$alkenyl-;
$R_2$ and $R_5$ are —C≡CH;
$R_6$ and $R_7$ are independently $C_1$-$C_6$alkyl, $C_2$-$C_6$alkenyl, $C_2$-$C_6$ alkynyl or $C_3$-$C_6$ cycloalkyl;
$R_8$ and $R_9$ are independently hydrogen, —OH, —$NH_2$, —$NO_3$, halogen, $C_1$-$C_6$alkyl, $C_2$-$C_6$alkenyl, $C_2$-$C_6$ alkynyl, $C_3$-$C_6$ cycloalkyl, $C_6$-$C_{14}$ aryl, 5-6-membered heteroaryl or 3-6 membered heterocyclyl.

In some embodiments, $R_1$ is hydroxyl.
In some embodiments, $R_1$ is —OC(O)$R^{1a}$, wherein $R^{1a}$ is $C_1$-$C_6$alkyl. In some embodiments, $R^{1a}$ is $C_1$-$C_4$alkyl, for example, methyl, ethyl, 1-propyl (n-Pr, n-propyl, —$CH_2CH_2CH_3$), 2-propyl (i-Pr, i-propyl, —$CH(CH_3)_2$), 1-butyl. In some embodiments, $R^{1a}$ is $C_1$-$C_3$alkyl or $C_1$-$C_2$alkyl. In some embodiments, $R^{1a}$ is ethyl.

In some embodiments, $R_1$ is —OC(O)$R^bCOOH$, wherein $R^{1b}$ is —$C_1$-$C_6$alkyl-. In some embodiments, $R_1$ is —OC(O)$R^{1b}$COOH, wherein $R^{1b}$ is —$C_2$-$C_6$alkenyl-. In some embodiments, $R_1$ is —OC(O)$R^{1b}$COOH, wherein $R^{1b}$ is methylene (i.e., —$CH_2$—) and $R_1$ is —OC(O)$CH_2$COOH. To give some examples of a salt form, in certain embodiments, $R_1$ is —OC(O)$CH_2$COOLi, —OC(O)$CH_2$COONa or —OC(O)$CH_2$COOK. In some embodiments, $R_1$ is —OC(O)$R^{1b}$COOH, wherein $R^{1b}$ is ethylene (i.e., —$CH_2CH_2$—) and $R_1$ is —OC(O)$CH_2CH_2$COOH. In certain embodiments, $R_1$ is —OC(O)$CH_2CH_2$COOLi, —OC(O)$CH_2CH_2$COONa or —OC(O)$CH_2CH_2$COOK. In some embodiments, $R_1$ is —OC(O)$R^{1b}$COOH, wherein $R^{1b}$ is —CH=CH— and $R_1$ is —OC(O)CH=CHCOOH. In certain embodiments, $R_1$ is —OC(O) CH=CHCOOLi, —OC(O) CH=CHCOONa or —OC(O) CH=CHCOOK.

In some embodiments, $R_4$ is hydroxyl.
In some embodiments, $R_4$ is —OC(O)$R^{4a}$, wherein $R^{4a}$ is $C_1$-$C_6$alkyl. In some embodiments, $R^{4a}$ is $C_1$-$C_4$alkyl, for example, methyl, ethyl, 1-propyl (n-Pr, n-propyl, —$CH_2CH_2CH_3$), 2-propyl (i-Pr, i-propyl, —$CH(CH_3)_2$), 1-butyl. In some embodiments, $R^{4a}$ is $C_1$-$C_3$alkyl or $C_1$-$C_2$alkyl. In some embodiments, $R^{4a}$ is ethyl.

In some embodiments, $R_4$ is —OC(O)$R^{4b}$COOH, wherein $R^{4b}$ is —$C_1$-$C_6$alkyl-. In some embodiments, $R_4$ is —OC(O)$R^{4b}$COOH, wherein $R^{4b}$ is —$C_2$-$C_6$alkenyl-. In some embodiments, $R_4$ is —OC(O)$R^{4b}$COOH, wherein $R^{4b}$ is methylene (i.e., —$CH_2$—) and $R_4$ is —OC(O)$CH_2$COOH. To give some examples of a salt form, in certain embodiments, $R_4$ is —OC(O)$CH_2$COOLi, —OC(O)$CH_2$COONa or —OC(O)$CH_2$COOK. In some embodiments, $R_4$ is —OC(O)$R^{4b}$COOH, wherein $R^{4b}$ is ethylene (i.e., —$CH_2CH_2$—) and $R_1$ is —OC(O)$CH_2CH_2$COOH. In certain embodiments, $R_4$ is —OC(O)$CH_2CH_2$COOLi, —OC(O)$CH_2CH_2$COONa or —OC(O)$CH_2CH_2$COOK. In some embodiments, $R_4$ is —OC(O)$R^{4b}$COOH, wherein $R^{4b}$ is —CH=CH— and $R_4$ is —OC(O)CH=CHCOOH. In certain embodiments, $R_4$ is —OC(O) CH=CHCOOLi, —OC(O) CH=CHCOONa or —OC(O) CH=CHCOOK.

In some embodiments, $R_6$ is $C_1$-$C_6$alkyl. In some embodiments, $R_6$ is $C_2$-$C_6$alkenyl. In some embodiments, $R_7$ is $C_1$-$C_6$alkyl. In some embodiments, $R_7$ is $C_2$-$C_6$alkenyl. $R_6$ and $R_7$ may or may not be the same.

In some embodiments, $R_8$ is hydrogen, —OH, —$NH_2$, —$NO_3$, halogen, $C_1$-$C_6$alkyl, or $C_2$-$C_6$alkenyl. In some embodiments, $R_8$ is hydrogen. In some embodiments, $R_8$ is $C_1$-$C_6$alkyl. In some embodiments, $R_9$ is hydrogen, —OH, —$NH_2$, —$NO_3$, halogen, $C_1$-$C_6$alkyl, or $C_2$-$C_6$alkenyl. In some embodiments, $R_9$ is hydrogen. In some embodiments, $R_9$ is $C_1$-$C_6$alkyl. $R_8$ and $R_9$ may or may not be the same.

A substantially pure diastereomeric compound described herein or a salt thereof can be prepared using a method comprising reacting a di-ketone compound of formula (II)

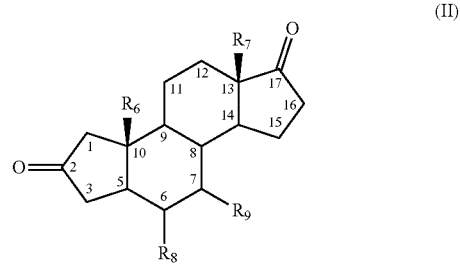

(II)

with silylacetylene of formula (III)

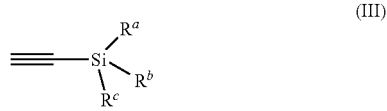

(III)

in the presence of an organometallic reagent $R_{10}$-M.

$R_6$, $R_7$, $R_8$ and $R_9$ of a di-ketone compound of formula (II) are as defined above in various embodiments of a compound has the structure of Formula (I).

With reference to the reaction step III-2 in Method II as illustrated in EXAMPLES below, an exemplary process to prepare α-anordrin comprising reacting a di-ketone product (c) with a silylacetylene, trimethylsilylacetylene (TMS). It was recognized in the present application, a silylacetylene can be used for asymmetric alkynylation of a de-ketone compound described herein. Without being bound to any particular theory, it is believed that two terminal alkynes add to two carbonyl groups of the de-ketone compound one by one.

$R^a$, $R^b$ and $R^c$ of silylacetylene of formula (III) can be the same or different. In some embodiments, $R^a$, $R^b$ and $R^c$ are independently selected from the group consisting of hydrogen, —OH, $C_1$-$C_{20}$alkyl optionally substituted by —OH, halogen or $C_1$-$C_6$alkyl, $C_1$-$C_6$alkoxy optionally substituted by —OH, halogen or $C_1$-$C_6$alkyl, $C_3$-$C_6$ cycloalkyl, $C_6$-$C_{14}$ aryl, 5-6-membered heteroaryl or 3-6 membered heterocyclyl. In some embodiments, $R^a$, $R^b$ and $R^c$ are independently $C_1$-$C_{20}$alkyl optionally substituted by —OH, halogen or $C_1$-$C_6$alkyl. In some embodiments, $R^a$, $R^b$ and $R^c$ are independently $C_1$-$C_6$alkyl, for example, methyl, ethyl, 1-propyl (n-Pr, n-propyl, —$CH_2CH_2CH_3$), 2-propyl (i-Pr, i-propyl, —$CH(CH_3)_2$), 1-butyl. In some embodiments, $R^a$, $R^b$ and $R^c$ are methyl and thus the silylacetylene is trimethylsilylacetylene (TMS). Without being bound to any particular theory, it is believed that one or more of $R^a$, $R^b$ and $R^c$ has a large size to create steric hindrance that leads to forming one diastereomer in preference to another.

An organometallic reagent used in accordance with the present methods is defined as $R_{10}$-M, wherein M is a metal. To give an example, $R_{10}$-M is n-Butyllithium.

In some embodiments, M is Li, Na or K. In some embodiments, M is Li.

In some embodiments, $R_{10}$ is $C_1$-$C_{20}$alkyl, optionally substituted by —OH, halogen, or $C_1$-$C_6$alkyl. In some embodiments, $R_{10}$ is $C_1$-$C_6$alkyl. In some embodiments, $R_{10}$ is n-butyl.

In some embodiments, tetramethylehtylenediamine (TEMED) is added with the organometallic reagent.

Methods provided herein, in various embodiments, are carried out in the presence of an organic solvent. A non-limiting list of suitable organic solvents includes, without limitation, dichloromethane, chloroform, acetoniltrile, dichloroethane, tetrahydrofuran (THF), dimethylsulfoxide, and toluene.

Methods provided herein are carried out under relatively low reaction temperature. A reaction temperature can range from a temperature of from about 00 to about –100° C. In some embodiments, a reaction temperature is between about –20° to about –90° C. In some embodiments, a reaction temperature is between about –40° to about –80° C. In some embodiments, a reaction temperature is between about –30° to about –50° C.

In accordance with some embodiments of the present invention, a method for stereospecifically preparing a substantially pure diastereomeric compound or a salt thereof further involves removing a silyl group of formula (IV):

(IV)

In some embodiments, the removing step is carried out by contacting with a deprotective agent. A non-limiting list of suitable deprotective agents includes, without limitation, tetrabutyl ammonium fluoride (TBAF), hydrofluoric acid and potassium fluoride.

Pharmaceutical Compositions and Formulations

The present disclosure includes a specific diastereomeric form of compounds described herein. Also provided are salts of compounds referred to herein, such as pharmaceutically acceptable salts. All forms of diastereomeric compounds are also embraced by the invention, such as crystalline or non-crystalline forms of the diastereomeric compounds. Compositions comprising a diastereomeric compound of the invention or a salt thereof are also intended, such as a composition of substantially pure diastereomeric compound or a salt thereof.

Pharmaceutical compositions of any of the diastereomeric compounds detailed herein are embraced by this disclosure. The present disclosure includes pharmaceutical compositions comprising a substantially pure diastereomeric compound of formula (I) or salt thereof and a pharmaceutically acceptable carrier or excipient. In one aspect, a salt is a pharmaceutically acceptable salt. For example, a salt is an acid addition salt, such as a salt formed with an inorganic or organic acid. Pharmaceutical compositions may take a form suitable for oral, buccal, parenteral, nasal, topical or rectal administration or a form suitable for administration by inhalation.

In one variation, substantially pure diastereomeric compounds or salts thereof are synthetic products prepared for administration to an individual. In another variation, compositions are provided containing a substantially pure diastereomeric compound or a salt thereof. In another variation, the present disclosure embraces pharmaceutical compositions comprising a compound detailed herein and a pharmaceutically acceptable carrier.

A diastereomeric compound detailed herein or salt thereof may be formulated for any available delivery route, including an oral, mucosal (e.g., nasal, sublingual, vaginal, buccal or rectal), parenteral (e.g., intramuscular, subcutaneous or intravenous), topical or transdermal delivery form. A diastereomeric compound or salt thereof may be formulated with suitable carriers to provide delivery forms that include, but are not limited to, tablets, caplets, capsules (such as hard gelatin capsules or soft elastic gelatin capsules), cachets, troches, lozenges, gums, dispersions, suppositories, ointments, cataplasms (poultices), pastes, powders, dressings, creams, solutions, patches, aerosols (e.g., nasal spray or inhalers), gels, suspensions (e.g., aqueous or non-aqueous liquid suspensions, oil-in-water emulsions or water-in-oil liquid emulsions), solutions and elixirs.

A diastereomeric compound described herein or a salt thereof can be used in the preparation of a formulation, such as a pharmaceutical formulation, by combining the compound or a salt thereof, as an active ingredient with a pharmaceutically acceptable carrier, such as those mentioned above. Depending on the therapeutic form of the system (e.g., transdermal patch vs. oral tablet), the carrier may be in various forms. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants. Formulations comprising the compound may also contain other substances which have valuable therapeutic properties. Pharmaceutical formulations may be prepared by known pharmaceutical methods. Suitable formulations can be found, e.g., in *Remington's Pharmaceutical Sciences*, Mack Publishing Company, Philadelphia, PA, 20$^{th}$ ed. (2000), which is incorporated herein by reference.

In some embodiments, diastereomeric compounds as described herein may be administered to individuals in a form of generally accepted oral compositions, such as tablets, coated tablets, and gel capsules in a hard or in soft shell, emulsions or suspensions. Examples of carriers, which may be used for the preparation of such compositions, are lactose, corn starch or its derivatives, talc, stearate or its salts, etc. Acceptable carriers for gel capsules with soft shell are, for instance, plant oils, wax, fats, semisolid and liquid poly-ols, and so on. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants.

Any of the diastereomeric compounds described herein or salts thereof can be formulated in a tablet in any dosage form described, for example, a compound as described herein or a pharmaceutically acceptable salt thereof can be formulated as a 10 mg tablet.

Methods of Use

Compounds and compositions detailed herein, such as a pharmaceutical composition containing a diastereomeric compound of formula (I) provided herein or a salt thereof and a pharmaceutically acceptable carrier or excipient, may be used in methods of administration and treatment as provided herein.

Estrogen deficiency is associated with the development of many health conditions, such as infertility, premature aging, osteoporosis and cardiovascular disease. Ovariectomized (OVX) or postmenopausal individuals typically suffer estrogen deficiency. Estrogen deficiency symptoms described herein include, but are not limited to, osteoporosis, fat liver, weight gain, high blood triglyceride and blood glucose, and organ atrophy (e.g., kidney, muscle and vulvovagina atrophy).

In some embodiments, there are provided methods of treatment of estrogen deficiency in an individual, comprising administering to the individual an effective amount of a diastereomeric compound of formula (I) (such as α-anordrin) or salt thereof.

In some embodiments, there are provided methods of preventing or reducing an estrogen deficiency symptom in an individual, comprising administering to an individual an effective amount of a diastereomeric compound of formula (I) (such as α-anordrin) or salt thereof. In some embodiments, provided are methods of preventing or reducing an estrogen deficiency symptom selected from the group consisting of high liver triglyceride, osteoporosis, vulvovagina atrophy, high blood triglyceride, high blood glucose and weight gain.

Without being bound to any particular theory, it is observed that a diastereomeric compound of formula (I) or salt thereof as detailed herein has a therapeutic effect that other stereochemical forms do not have. Therefore, a diastereomeric compound of formula (I), compositions and method thereof as detailed in the present application may have an advantageous therapeutic effect as compare to other sterochemical forms or a sterochemical mixture of a compound of formula (I). To give one specific example, two chiral anordrin compounds were found, which are named as 2alpha-(α-) and 2beta- (β-) anordrin (18, 19). In accordance with some embodiments of the present invention, α-anordrin has a therapeutic effect in treatment of estrogen deficiency and in preventing or reducing an estrogen deficiency symptom, while β-anordrin has no minimal therapeutic effect in these treatments.

In some aspects, provided herein is a combination therapy in which a diastereomeric compound of formula (I) (such as α-anordrin) or salt thereof is coadministered (which may be separately or simultaneously) with one or more additional agents. For example, a diastereomeric compound of formula (I) or salt thereof, and one or more additional agents are administered simultaneously (for example in a single composition, such as the pharmaceutical compositions described herein). Additionally or alternatively, a diastereomeric compound of formula (I) or salt thereof, and one or more additional agents can be administered sequentially, such as one or more additional agents being administered first and a diastereomeric compound of formula (I) or salt thereof second, or a diastereomeric compound of formula (I) or salt thereof being administered first and one or more additional agents second.

The present disclosure include methods of treatment of estrogen deficiency, as well as methods of preventing or reducing an estrogen deficiency symptom, comprising administering a diastereomeric compound of formula (I) (such as α-anordrin) or salt thereof, in combination with at least one additional agent. Additional agents can be selective estrogen receptor modulators (SERMs) and aromatase inhibitors.

SERMs are now being used as a treatment for breast cancer, osteoporosis and postmenopausal symptoms, as these drugs have features that can act as an estrogen agonist and an antagonist, depending on the target tissue. In accordance with the present invention, suitable SERMs include, but not limited to, tamoxifen, raloxifene, toremifene, lasofoxifene, bazedoxifene, arzoxifene, ormeloxifene, ospemifene, and levormeloxifene. In some embodiments, the SERM used in combination with a diastereomeric compound as detailed herein or salt thereof, is tamoxifen. In some embodiments, the SERM used in combination with a diastereomeric compound as detailed herein or salt thereof, is raloxifene or a functional equivalent thereof. "Functional equivalent thereof" used herein refers to compounds that functions through the same mechanism as raloxifene. For example, functional equivalents of raloxifene include, but are not limited to, lasofoxifene, bazedoxifene, arzoxifene, ormeloxifene, ospemifene, and levormeloxifene.

In some embodiments, a method of treatment of estrogen deficiency comprising administering a diastereomeric compound of formula (I) (such as α-anordrin) or salt thereof, in combination with at least one SERM. In some embodiments, a method of preventing or reducing an estrogen deficiency symptom comprising administering a diastereomeric compound (such as α-anordrin) or salt thereof, in combination with at least one SERMs.

"Aromatase inhibitor" refers to a class of agents that inhibit aromatase activity. Aromatase inhibitors have been used in the treatment of breast cancer and ovarian cancer in postmenopausal women to reduce increase of estrogen conversion during cycle with external testosterone. Suitable aromatase inhibitors include, but are not limited to, anastrozole (Arimidex), letrozole (Femara), exemestane (Aromasin), vorozole (Rivizor), formestane (Lentaron), and fadrozole (Afema). In some embodiments, the aromatase inhibitor used in combination with a diastereomeric compound as detailed herein or salt thereof, is anastrozole.

In some embodiments, a method of treatment of estrogen deficiency comprising administering a diastereomeric compound of formula (I) (such as α-anordrin) or salt thereof, in combination with at least one aromatase inhibitor. In some embodiments, a method of preventing or reducing an estrogen deficiency symptom comprising administering a diastereomeric compound (such as α-anordrin) or salt thereof, in combination with at least one aromatase inhibitors.

In some embodiments, there is provided a method of preventing or reducing osteoporosis in an individual, comprising administering to the individual an effective amount of a diastereomeric compound of formula (I) or salt thereof.

In some embodiments, there is provided a method of preventing or reducing osteoporosis in an individual, comprising administering to the individual: a) an effective amount of a diastereomeric compound of formula (I) or salt thereof; and b) an effective amount of at least one additional agent, wherein the additional agent is raloxifene or functional equivalent thereof. In some embodiments, the additional agent is raloxifene.

In some embodiments, there is provided a method of preventing or reducing osteoporosis in an individual, comprising administering to the individual: a) an effective amount of a diastereomeric compound of formula (I) or salt thereof; and b) an effective amount of at least one additional agent, wherein the additional agent is an aromatase inhibitor. In some embodiments, the additional agent is anastrozole.

In some embodiments, the method preventing or reducing osteoporosis further comprises administering to the individual an effective amount of calcium. Suitable amounts of calcium include, but are not limited to, about 0.25 to about 500 mg/day, such as about 10 to about 200 mg/day, about 50 to about 1500 mg/day. In some embodiments, the method further comprises administering to the individual an effective amount of vitamin D. Suitable amounts of vitamin D include, but are not limited to, about 400 to about 800 IU/day, such as about 500 to about 600 IU/day.

In some embodiments, there is provided a method of preventing or reducing high liver triglyceride in an individual, comprising administering to the individual an effective amount of a diastereomeric compound of formula (I) or salt thereof.

In some embodiments, there is provided a method of preventing or reducing high liver triglyceride in an individual, comprising administering to the individual: a) an effective amount of a diastereomeric compound of formula (I) or salt thereof; and b) an effective amount of at least one additional agent, wherein the additional agent is raloxifene or functional equivalent thereof. In some embodiments, the additional agent is raloxifene. In some embodiments, the additional agent is selected from the group consisting of tamoxifen, raloxifene, lasofoxifene, bazedoxifene, arzoxifene, ormeloxifene, ospemifene, and levormeloxifene.

In some embodiments, there is provided a method of preventing or reducing high blood glucose in an individual, comprising administering to the individual an effective amount of a diastereomeric compound of formula (I) or salt thereof.

In some embodiments, there is provided a method of preventing or reducing high blood glucose in an individual, comprising administering to the individual: a) an effective amount of a diastereomeric compound of formula (I) or salt thereof; and b) an effective amount of at least one additional agent, wherein the additional agent is raloxifene or functional equivalent thereof. In some embodiments, the additional agent is raloxifene. In some embodiments, the additional agent is selected from the group consisting of tamoxifen, raloxifene, lasofoxifene, bazedoxifene, arzoxifene, ormeloxifene, ospemifene, and levormeloxifene.

In some embodiments, there is provided a method of preventing or reducing vulvovaginal atrophy in an individual, comprising administering to the individual an effective amount of a diastereomeric compound of formula (I) or salt thereof.

In some embodiments, there is provided a method of preventing or reducing vulvovaginal atrophy in an individual, comprising administering to the individual: a) an effective amount of a diastereomeric compound of formula (I) or salt thereof; and b) an effective amount of at least one additional agent, wherein the additional agent is raloxifene or functional equivalent thereof. In some embodiments, the additional agent is raloxifene. In some embodiments, the additional agent is selected from the group consisting of tamoxifen, raloxifene, lasofoxifene, bazedoxifene, arzoxifene, ormeloxifene, ospemifene, and levormeloxifene.

In some embodiments, there is provided a method of preventing or reducing vulvovaginal atrophy in an individual, comprising administering to the individual: a) an effective amount of a diastereomeric compound of formula (I) or salt thereof; and b) an effective amount of at least one additional agent, wherein the additional agent is an aromatase inhibitor. In some embodiments, the additional agent is selected, but not limited, from the group consisting of anastrozole or functional equivalent thereof.

In some embodiments, there is provided a method of preventing or reducing weight gain in an individual, comprising administering to the individual an effective amount of a diastereomeric compound of formula (I) or salt thereof.

In some embodiments, there is provided a method of preventing or reducing weight gain in an individual, comprising administering to the individual: a) an effective amount of a diastereomeric compound of formula (I) or salt thereof; and b) an effective amount of at least one additional agent, wherein the additional agent is raloxifene or functional equivalent thereof. In some embodiments, the additional agent is raloxifene. In some embodiments, the additional agent is selected from the group consisting of tamoxifen, raloxifene, lasofoxifene, bazedoxifene, arzoxifene, ormeloxifene, ospemifene, and levormeloxifene.

In some embodiments, there is provided a method of preventing or reducing high blood triglyceride in an individual, comprising administering to the individual an effective amount of a diastereomeric compound of formula (I) or salt thereof.

In some embodiments, there is provided a method of preventing or reducing high blood triglyceride in an individual, comprising administering to the individual: a) an effective amount of a diastereomeric compound of formula (I) or salt thereof; and b) an effective amount of at least one additional agent, wherein the additional agent is raloxifene or functional equivalent thereof. In some embodiments, the additional agent is raloxifene. In some embodiments, the additional agent is selected from the group consisting of tamoxifen, raloxifene, lasofoxifene, bazedoxifene, arzoxifene, ormeloxifene, ospemifene, and levormeloxifene.

In certain embodiment, provided herein is a method of preventing or reducing high liver triglyceride in an individual, comprising administering to the individual an effective amount of a substantially pure diastereomeric compound being (2α,17β)-diethynyl-(2β, 17β)-diol-dipropionate-A-nor-5α-androstane (α-anordrin) of formula (Ia)

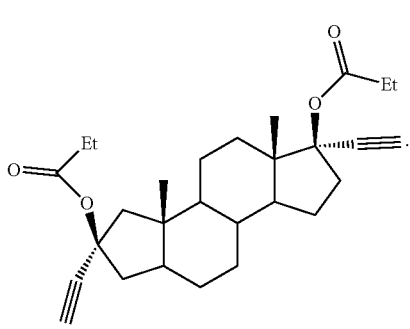

In certain embodiment, provided herein is a method of preventing or reducing high blood triglyceride in an individual, comprising administering to the individual an effective amount of a substantially pure diastereomeric compound being (2α,17α)-diethynyl-(2β, 17β)-diol-dipropionate-A-nor-5α-androstane (α-anordrin) of formula (Ia)

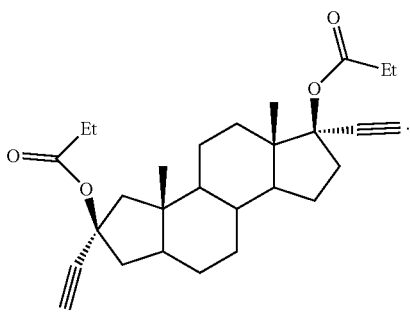

In certain embodiment, provided herein is a method of preventing or reducing osteoporosis in an individual, comprising administering to the individual an effective amount of a substantially pure diastereomeric compound being (2α,17α)-diethynyl-(2β, 17β)-diol-dipropionate-A-nor-5α-androstane (α-anordrin) of formula (Ia)

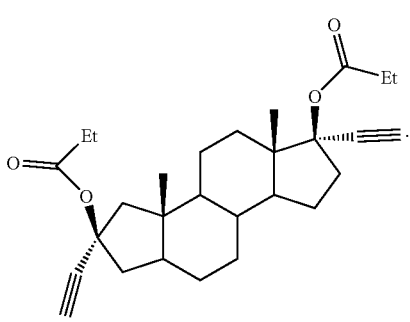

In certain embodiment, provided herein is a method of preventing or reducing vulvovagina atrophy in an individual, comprising administering to the individual an effective amount of a substantially pure diastereomeric compound being (2α, 17α)-diethynyl-(2β, 17β)-diol-dipropionate-A-nor-5α-androstane (α-anordrin) of formula (Ia)

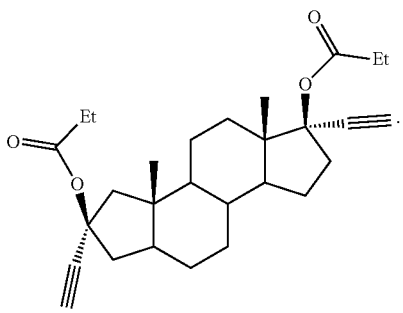

In certain embodiment, provided herein is a method of preventing or reducing high blood glucose in an individual, comprising administering to the individual an effective amount of a substantially pure diastereomeric compound being (2α,17α)-diethynyl-(2β, 17β)-diol-dipropionate-A-nor-5α-androstane (α-anordrin) of formula (Ia)

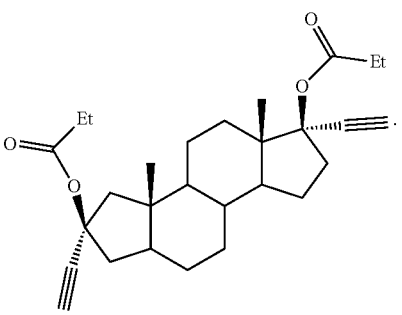

In certain embodiment, provided herein is a method of preventing or reducing weight gain in an individual, comprising administering to the individual an effective amount of a substantially pure diastereomeric compound being (2α,17α)-diethynyl-(2β, 17β)-diol-dipropionate-A-nor-5α-androstane (α-anordrin) of formula (Ia)

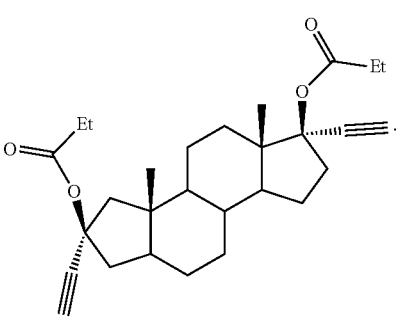

In the methods described above, the substantially pure diastereomeric compound has a diastereomeric excess (de) of no less than about 98%.

In the methods described above, the substantially pure diastereomeric compound has a diastereomeric excess (de) of no less than about 99%, about 99.5%, or about 99.9%.

However, the side effects as seen with traditional estrogen replacement therapy (ERT) as well as aromatase inhibitors and SERMs are still a concern to some investigators (12). Tamoxifen was marketed as an antagonist of the estrogen classical pathway to treat breast cancer patients, and was also reported as an agonist of ER-α36, potentially leading to anti-estrogen therapy resistance while stimulating the growth of endometrial epithelium cells, resulting in endometrium cancer (7, 8). Raloxifene was marketed as an upgraded version of tamoxifen, having fewer side effects and the advantages of preventing postmenopausal symptoms, such as osteoporosis. However, raloxifene can still cause serious side effects common to tamoxifen treatment, such as thromboembolism and non-alcohol steatohepatitis (NASH) (9,10). The detailed mechanisms responsible for the side effects caused by either raloxifene or tamoxifen are still unclear. Ipriflavone is a derivative of phytohormone, and its metabolite binds to the ER-α LBD with a lower affinity than E2, exhibiting reduced estrogenic effects. The metabolites of ipriflavone and isoflavone show comparable binding affinity and activity with ER-β as well as E2, and they have been utilized in some countries as a medicine to prevent osteoporosis. Their effectiveness was not supported in at least one clinical trial (11). Moreover, aromatase inhibitors were landed for ER-positive breast cancer in postmenopausal women. It also inhibited the synthesis of estrogen in bone resulting in osteoporosis.

Provided herein is a method of reducing a side effect of at least one additional agent in an individual, comprising administering to the individual an effective amount of a diastereomeric compound of formula (I) or salt thereof when used in combination with the at least one additional agent. In some embodiments, a diastereomeric compound of formula (I) or salt thereof used in combination with a tamoxifen can reduce a side effect of tamoxifen. For example, it is observed in the present application that α-anordrin used in combination with tamoxifen reduces a side effect of tamoxifen, resulting in effective combination therapy for treatment of estrogen deficiency or in preventing or reducing an estrogen deficiency symptom. In some embodiments, a diastereomeric compound of formula (I) or salt thereof used in combination with at least one aromatase inhibitor can reduce a side effect of the aromatase inhibitor.

In certain embodiment, provided herein is a method of reducing a side effect of tamoxifen in an individual, comprising administering to the individual an effective amount of a substantially pure diastereomeric compound being (2α,17α)-diethynyl-(2β, 17β)-diol-dipropionate-A-nor-5α-androstane (α-anordrin) of formula (Ia)

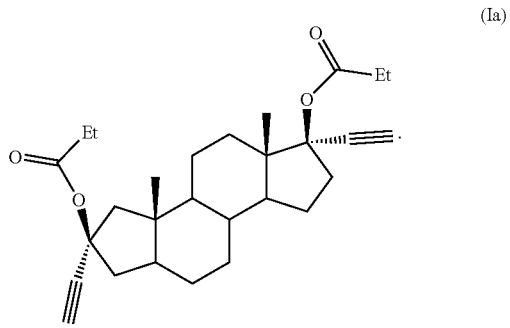 [SMILES: C#C[C@@]1(OC(=O)CC)CC2CCC3C(CC[C@@]4(C)C3CC[C@]4(C#C)OC(=O)CC)[C@@]2(C)C1]

in combination with tamoxifen.

In certain embodiment, provided herein is a method of reducing a side effect of at least one aromatase inhibitor in an individual, comprising administering to the individual an effective amount of a substantially pure diastereomeric compound being (2α, 17α)-diethynyl-(2β, 17β)-diol-dipropionate-A-nor-5α-androstane (α-anordrin) of formula (Ia)

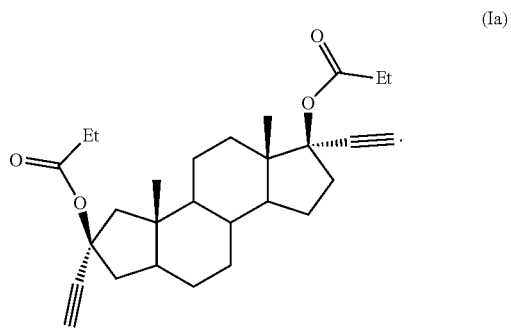 [SMILES: C#C[C@@]1(OC(=O)CC)CC2CCC3C(CC[C@@]4(C)C3CC[C@]4(C#C)OC(=O)CC)[C@@]2(C)C1]

in combination with the aromatase inhibitor.

In the methods described above, the substantially pure diastereomeric compound has a diastereomeric excess (de) of no less than about 98%.

In the methods described above, the substantially pure diastereomeric compound has a diastereomeric excess (de) of no less than about 99%, about 99.5%, or about 99.9%.

Modes of Administration

In the context of combination therapy, the compositions comprising a diastereomeric compound of formula (I) or salt thereof and the additional agent can be administered simultaneously (i.e., simultaneous administration) and/or sequentially (i.e., sequential administration).

In some embodiments, a diastereomeric compound of formula (I) or salt thereof and the additional agent (including the specific agents described herein) are administered simultaneously. The term "simultaneous administration," as used herein, means that the diastereomeric compound of formula (I) or salt thereof and the additional agent are administered with a time separation of no more than about 15 minute(s), such as no more than about any of 10, 5, or 1 minutes. When the drugs are administered simultaneously, the diastereomeric compound of formula (I) or salt thereof and the additional agent may be contained in the same composition (e.g., a composition comprising both the diastereomeric compound of formula (I) or salt thereof and the additional agent, for example the pharmaceutical composition comprised herein) or in separate compositions (e.g., a diastereomeric compound of formula (I) or salt thereof and the additional agent are contained in separate compositions).

In some embodiments, a diastereomeric compound of formula (I) or salt thereof and the additional agent are administered sequentially. The term "sequential administration" as used herein means that the diastereomeric compound of formula (I) or salt thereof and the additional agent are administered with a time separation of more than about 15 minutes, such as more than about any of 20, 30, 40, 50, 60 or more minutes. Either a diastereomeric compound of formula (I) or salt thereof or the additional agent may be administered first. A diastereomeric compound of formula (I) or salt thereof and the additional agent are contained in separate compositions, which may be contained in the same or different packages.

In some embodiments, the administration of a diastereomeric compound of formula (I) or salt thereof and the additional agent are concurrent, i.e., the administration period of the diastereomeric compound of formula (I) or salt thereof and that of the additional agent overlap with each other. In some embodiments, the diastereomeric compound of formula (I) or salt thereof is administered for at least one cycle (for example, at least any of 2, 3, or 4 cycles) prior to the administration of the additional agent. In some embodiments, the additional agent is administered for at least any of one, two, three, or four weeks. In some embodiments, the administrations of the diastereomeric compound of formula (I) or salt thereof and the additional agent are initiated at about the same time (for example, within any one of 1, 2, 3, 4, 5, 6, or 7 days). In some embodiments, the administrations of the diastereomeric compound of formula (I) or salt thereof and the additional agent are terminated at about the same time (for example, within any one of 1, 2, 3, 4, 5, 6, or 7 days). In some embodiments, the administration of the additional agent continues (for example for about any one of 1, 2, 3, 4, 5, 6, 7, 8, 9, 10, 11, or 12 months) after the termination of the administration of the diastereomeric compound of formula (I) or salt thereof. In some embodiments, the administration of the additional agent is initiated after (for example after about any one of 1, 2, 3, 4, 5, 6, 7, 8, 9, 10, 11, or we months) the initiation of the administration of the diastereomeric compound of formula (I) or salt thereof. In some embodiments, the administrations of the diastereomeric compound of formula (I) or salt thereof and the additional agent are initiated and terminated at about the same time. In some embodiments, the administrations of the diastereomeric compound of formula (I) or salt thereof and the additional agent are initiated at about the same time and the administration of the additional agent continues (for example for about any one of 1, 2, 3, 4, 5, 6, 7, 8, 9, 10, 11, or 12 months) after the termination of the administration of the diastereomeric compound of formula (I) or salt thereof. In some embodiments, the administration of the diastereomeric compound of formula (I) or salt thereof and the additional agent stop at about the same time and the administration of the additional agent is initiated after (for example after about any one of 1, 2, 3, 4, 5, 6, 7, 8, 9, 10, 11, or we months) the initiation of the administration of the diastereomeric compound of formula (I) or salt thereof.

The dosing frequency of a diastereomeric compound of formula (I) or salt thereof and/or the additional agent may be adjusted over the course of the treatment, based on the judgment of the administering physician. When administered separately, a diastereomeric compound of formula (I) or salt thereof and the additional agent can be administered at different dosing frequency or intervals. For example, a diastereomeric compound of formula (I) or salt thereof can be administered weekly, while an additional agent can be administered more or less frequently. Various formulations and devices for achieving sustained release are known in the art. Exemplary dosing frequencies are further provided herein.

A diastereomeric compound of formula (I) or salt thereof and the additional agent can be administered using the same route of administration or different routes of administration. Exemplary administration routes are further provided herein. In some embodiments (for both simultaneous and sequential administrations), a diastereomeric compound of formula (I) or salt thereof and the additional agent are administered at a predetermined ratio. For example, in some embodiments, the ratio by weight of a diastereomeric compound of formula (I) or salt thereof and the additional agent is about 1 to 1. In some embodiments, the weight ratio may be between about 0.001 to about 1 and about 1000 to about 1, or between about 0.01 to about 1 and 100 to about 1. In some embodiments, the ratio by weight of a diastereomeric compound of formula (I) or salt thereof and the additional agent is less than about any of 100:1, 50:1, 30:1, 10:1, 9:1, 8:1, 7:1, 6:1, 5:1, 4:1, 3:1, 2:1, and 1:1 In some embodiments, the ratio by weight of a diastereomeric compound of formula (I) or salt thereof and the additional agent is more than about any of 1:1, 2:1, 3:1, 4:1, 5:1, 6:1, 7:1, 8:1, 9:1, 30:1, 50:1, 100:1. Other ratios are contemplated.

The doses required for a diastereomeric compound of formula (I) or salt thereof and/or the additional agent may (but not necessarily) be lower than what is normally required when each agent is administered alone. Thus, in some embodiments, a subtherapeutic amount of a diastereomeric compound of formula (I) or salt thereof and/or the additional agent is administered. "Subtherapeutic amount" or "subtherapeutic level" refers to an amount that is less than therapeutic amount, that is, less than the amount normally used when a diastereomeric compound of formula (I) or salt thereof and/or the additional agent is administered alone. The reduction may be reflected in terms of the amount administered at a given administration and/or the amount administered over a given period of time (reduced frequency).

In some embodiments, enough additional agent is administered so as to allow reduction of the normal dose of a diastereomeric compound of formula (I) or salt thereof required to effect the same degree of treatment by at least about any of 5%, 10%, 20%, 30%, 50%, 60%, 70%, 80%, 90%, or more. In some embodiments, enough diastereomeric compound of formula (I) or salt thereof is administered so as to allow reduction of the normal dose of the additional agent required to effect the same degree of treatment by at least about any of 5%, 10%, 20%, 30%, 50%, 60%, 70%, 80%, 90%, or more.

In some embodiments, the doses of both a diastereomeric compound of formula (I) or salt thereof and the additional agent are reduced as compared to the corresponding normal dose of each when administered alone. In some embodiments, both a diastereomeric compound of formula (I) or salt thereof and the additional agent are administered at a subtherapeutic, i.e., reduced, level. In some embodiments, the dose of a diastereomeric compound of formula (I) or salt thereof and/or the additional agent is substantially less than the established maximum toxic dose (MTD). For example, the dose of a diastereomeric compound of formula (I) or salt thereof and/or the additional agent is less than about 50%, 40%, 30%, 20%, or 10% of the MTD.

In some embodiments, the dose of a diastereomeric compound of formula (I) or salt thereof and/or the dose of the additional agent is higher than what is normally required when each agent is administered alone. For example, in some embodiments, the dose of a diastereomeric compound of formula (I) or salt thereof and/or the additional agent is substantially higher than the established maximum toxic dose (MTD). For example, the dose of a diastereomeric compound of formula (I) or salt thereof and/or the additional agent is more than about 50%, 40%, 30%, 20%, or 10% of the MTD of the agent when administered alone.

In some embodiments, the amount of a diastereomeric compound of formula (I) or salt thereof (alone or in combination with an additional agent) is included in any of the following ranges: about 0.1 to about 0.5 mg, about 0.5 to about 5 mg, about 5 to about 10 mg, about 10 to about 15 mg, about 15 to about 20 mg, about 20 to about 25 mg, about 20 to about 50 mg, about 25 to about 50 mg, about 50 to about 75 mg, about 50 to about 100 mg, about 75 to about 100 mg, about 100 to about 125 mg, about 125 to about 150 mg, about 150 to about 175 mg, about 175 to about 200 mg, about 200 to about 225 mg, about 225 to about 250 mg, about 250 to about 300 mg, about 300 to about 350 mg, about 350 to about 400 mg, about 400 to about 450 mg, or about 450 to about 500 mg. In some embodiments, the amount of a diastereomeric compound of formula (I) or salt thereof (e.g., a unit dosage form) is in the range of about 5 mg to about 500 mg, such as about 30 mg to about 300 mg or about 50 mg to about 200 mg.

In some embodiments, the amount of a diastereomeric compound of formula (I) or salt thereof (alone or in combination with an additional agent) includes at least about any of 0.01 mg/kg, 0.05 mg/kg, 0.1 mg/kg, 0.25 mg/kg, 0.5 mg/kg, 1 mg/kg, 2.5 mg/kg, 3.5 mg/kg, 5 mg/kg, 6.5 mg/kg, 7.5 mg/kg, 10 mg/kg, 15 mg/kg or 20 mg/kg. In some embodiments, the amount of a diastereomeric compound of formula (I) or salt thereof (alone or in combination with an additional agent) includes at least about any of 0.01 mg/kg/day, 0.05 mg/kg/day, 0.1 mg/kg/day, 0.25 mg/kg/day, 0.5 mg/kg/day, 1 mg/kg/day, 2.5 mg/kg/day, 3.5 mg/kg/day, 5 mg/kg/day, 6.5 mg/kg/day, 7.5 mg/kg/day, 10 mg/kg/day, 15 mg/kg/day or 20 mg/kg/day.

In some embodiments, the amount of the additional agent includes at least about any of 0.01 mg/kg, 0.05 mg/kg, 0.1 mg/kg, 0.25 mg/kg, 0.5 mg/kg, 1 mg/kg, 2.5 mg/kg, 3.5 mg/kg, 5 mg/kg, 6.5 mg/kg, 7.5 mg/kg, 10 mg/kg, 15 mg/kg or 20 mg/kg. In some embodiments, the amount of a diastereomeric compound of formula (I) or salt thereof (alone or in combination with an additional agent) includes at least about any of 0.01 mg/kg/day, 0.05 mg/kg/day, 0.1 mg/kg/day, 0.25 mg/kg/day, 0.5 mg/kg/day, 1 mg/kg/day, 2.5 mg/kg/day, 3.5 mg/kg/day, 5 mg/kg/day, 6.5 mg/kg/day, 7.5 mg/kg/day, 10 mg/kg/day, 15 mg/kg/day or 20 mg/kg/day.

Exemplary dosing frequencies for a diastereomeric compound of formula (I) or salt thereof (and for the additional agent) include, but are not limited to, once every 2 weeks, once every 3 weeks, once every 4 weeks, once every 6 weeks, or once every 8 weeks. In some embodiments, the composition is administered at least about any of 1×, 2×, 3×, 4×, 5×, 6×, or 7× (i.e., daily) a week, or three times daily, two times daily. In some embodiments, the intervals between each administration are less than about any of 6 months, 3 months, 1 month, 20 days, 15 days, 12 days, 10 days, 9 days, 8 days, 7 days, 6 days, 5 days, 4 days, 3 days, 2 days, or 1 day. In some embodiments, the intervals between each administration are more than about any of 1 month, 2 months, 3 months, 4 months, 5 months, 6 months, 8 months, or 12 months. In some embodiments, there is no break in the dosing schedule. In some embodiments, the interval between each administration is no more than about a week.

The administration of a diastereomeric compound of formula (I) or salt thereof (and for the additional agent) can be extended over an extended period of time, such as from about a month up to about seven years. In some embodiments, the composition is administered over a period of at least about any of 2, 3, 4, 5, 6, 7, 8, 9, 10, 11, 12, 18, 24, 30, 36, 48, 60, 72, or 84 months.

In some embodiments, the individual is treated for at least about any of one, two, three, four, five, six, seven, eight, nine, or ten treatment cycles.

The dosing frequency of the additional agent can be the same or different from that of a diastereomeric compound of formula (I) or salt thereof. Exemplary frequencies are provided above.

A diastereomeric compound of formula (I) or salt thereof (and the additional agent) described herein can be administered to an individual (such as human) via various routes, including, for example, oral, intravenous, intra-arterial, intraperitoneal, intrapulmonary, inhalation, intravesicular, intramuscular, intra-tracheal, subcutaneous, intraocular, intrathecal, transmucosal, and transdermal. In some embodiments, sustained continuous release formulation of the composition may be used.

A combination of the administration configurations described herein can be used. The combination therapy methods described herein may be performed alone or in conjunction with another therapy, such as surgery, radiation, chemotherapy, immunotherapy, gene therapy, and the like. Additionally, a person having a greater risk of developing the proliferative disease may receive treatments to inhibit or and/or delay the development of the disease.

As will be understood by those of ordinary skill in the art, the appropriate doses of additional agents will be approximately those already employed in clinical therapies wherein the additional agent are administered alone or in combination with additional agents. Variation in dosage will likely occur depending on the condition being treated. As described above, in some embodiments, the additional agents may be administered at a reduced level.

Kits and Medicines

The invention also provides medicine, kits, and unit dosages useful for methods described herein. Also provided are any use described herein whether in the context of use as a medicament and/or use for manufacture of a medicament.

Compositions in some embodiments may be present in a unit dosage form (such as an oral unit dosage form). Suitable unit dosage forms include, but are not limited to, capsules, tablets, pills, caplets, gels, liquids (e.g., suspensions, solutions, emulsions), powders or other particulates, and so forth.

In some embodiments, the ratio by weight of a diastereomeric compound of formula (I) or salt thereof and at least one additional agent in the composition is about 1 to 1. In some embodiments, the weight ratio is between about 0.001 to about 1 and about 1000 to about 1, or between about 0.01 to about 1 and 100 to about 1. In some embodiments, the ratio by weight of a diastereomeric compound of formula (I) or salt thereof and the additional agent is less than about any of 100:1, 50:1, 30:1, 10:1, 9:1, 8:1, 7:1, 6:1, 5:1, 4:1, 3:1, 2:1, and 1:1 In some embodiments, the ratio by weight of a diastereomeric compound of formula (I) or salt thereof and the additional agent is more than about any of 1:1, 2:1, 3:1, 4:1, 5:1, 6:1, 7:1, 8:1, 9:1, 30:1, 50:1, 100:1. In some embodiments, the weight ratio of a diastereomeric compound of formula (I) or salt thereof and the additional agent in the composition is about 1:20 to about 20:1 (including for example about 10:1 to about 1:10, or about 1:10 to about 1:15).

In another aspect, there are provided kits comprising a diastereomeric compound of formula (I) or salt thereof and the additional agent either in separate containers or in the same container. Kits of the invention include one or more containers comprising a diastereomeric compound of formula (I) or salt thereof (or unit dosage forms and/or articles of manufacture) and/or at least one additional agent, and in some embodiments, further comprise instructions for use in accordance with any of the methods described herein. The kit may further comprise a description of selection an individual suitable or treatment. Instructions supplied in the kits of the invention are typically written instructions on a label or package insert (e.g., a paper sheet included in the kit), but machine-readable instructions (e.g., instructions carried on a magnetic or optical storage disk) are also acceptable.

In some embodiments, the kit comprises a) an effective amount a diastereomeric compound of formula (I) or salt thereof, and b) an effective amount of at least one additional agent selected from the group consisting of tamoxifen, raloxifene or functional equivalent thereof, and an aromatase inhibitor. In some embodiments, the kit comprises: a) an effective amount a diastereomeric compound of formula (I) or salt thereof, and b) an effective amount of at least one additional agent selected from the group consisting of tamoxifen, raloxifene or functional equivalent thereof, and an aromatase inhibitor, and c) instructions for administering a diastereomeric compound of formula (I) or salt thereof and the additional agents simultaneously, sequentially, or concurrently for treatment of cancer (or other uses described herein).

A diastereomeric compound of formula (I) or salt thereof and the additional agents can be present in separate containers or in a single container. It is understood that the kit may comprise one distinct composition or two or more compositions wherein one composition comprises a diastereomeric compound of formula (I) or salt thereof and one composition comprises an additional agent.

The kits of the invention are in suitable packaging. Suitable packaging include, but is not limited to, vials, bottles, jars, flexible packaging (e.g., sealed Mylar or plastic bags), and the like. Kits may optionally provide additional components such as buffers and interpretative information. The present application thus also provides articles of manufacture, which include vials (such as sealed vials), bottles, jars, flexible packaging, and the like.

The instructions relating to the use of a diastereomeric compound of formula (I) or salt thereof generally include information as to dosage, dosing schedule, and route of administration for the intended treatment. The containers may be unit doses, bulk packages (e.g., multi-dose packages) or sub-unit doses. For example, kits may be provided that contain sufficient dosages of a diastereomeric compound of formula (I) or salt thereof as disclosed herein to provide effective treatment of an individual for an extended period, such as any of a week, 2 weeks, 3 weeks, 4 weeks, 6 weeks, 8 weeks, 3 months, 4 months, 5 months, 7 months, 8 months, 9 months, or more. Kits may also include multiple unit doses of a diastereomeric compound of formula (I) or salt thereof and pharmaceutical compositions and instructions for use and packaged in quantities sufficient for storage and use in pharmacies, for example, hospital pharmacies and compounding pharmacies.

Those skilled in the art will recognize that several embodiments are possible within the scope and spirit of this invention. The invention will now be described in greater detail by reference to the following non-limiting examples. The following examples further illustrate the invention but, of course, should not be construed as in any way limiting its scope.

EXAMPLES

Although the invention has been described and illustrated with a certain degree of particularity, it is understood that the present disclosure has been made only by way of example, and that numerous changes in the combination and arrangement of parts can be resorted to by those skilled in the art without departing from the spirit and scope of the invention, as defined by the claims.

Example 1: Synthetic Examples

Chemical synthesis of α-anordrin can be prepared as described in using steps detailed below method I (as shown in Scheme I), incorporated herein, or method II (scheme II) by reference U.S. Pat. No. 5,001,120, and the publication of Organic Letters, 2007, 9(9); 1643-6.

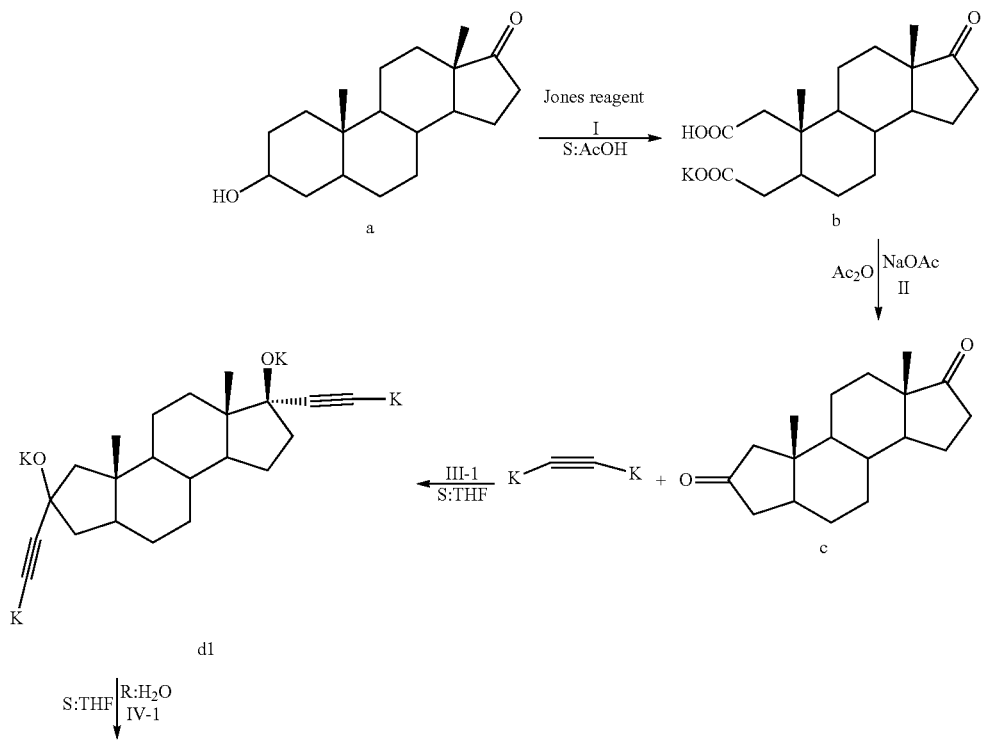

-continued

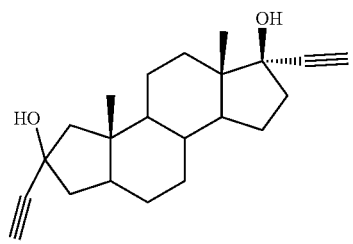

e

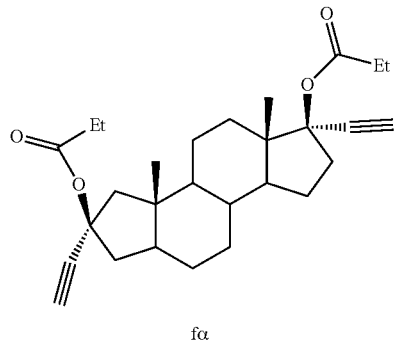

fα

+

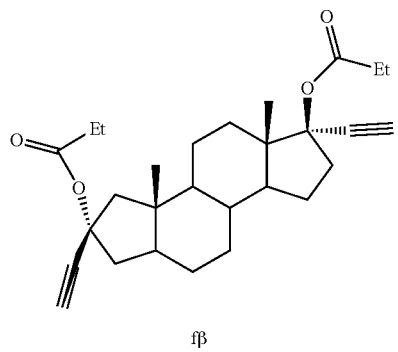

fβ

Reaction Step I:

Preparation of Jones reagent: 57 g CrO₃ was soluted in 400 ml H₂O, and then slowly added 85 ml H₂SO₄. The yielding Jones reagent was then colded to 40° C. 50 g of 5α-androstane and 200 ml of acetic acid were added into a 1 L three-necked flask. The mixture was warmed to 55-60° C., stirred and dissolved under nitrogen atmosphere. Jones reagent was added dropwise within 1 hour. Reaction temperature was increased to 90° C. and reacted for 1 hour, and acetic acid was distilled the reduced pressure. The residue was filtrated, washed with H₂O and dryed to give 50 g of di-acidic product (b).

Reaction Step I:

Preparation of Jones reagent: 57 g CrO₃ was soluted in 400 ml H₂O, and then slowly added 85 ml H₂SO₄. The yielding Jones reagent was then colded to 40° C. 50 g of 5α-androstane and 200 ml of acetic acid were added into a 1 L three-necked flask. The mixture was warmed to 55-60° C., stirred and dissolved under nitrogen atmosphere. Jones reagent was added dropwise within 1 hour. Reaction temperature was increased to 90° C. and reacted for 1 hour, and acetic acid was distilled the reduced pressure. The residue was filtrated, washed with H₂O and dryed to give 50 g of di-acidic product (b).

Reaction Step II:

30 g of di-acid product (b) and 600 mL of acetic anhydride were dissolved in 1 L three-necked flask and added in 24 g sodium acetate, stirred and refluxed for 4 hours. The residue was filtrated and dried and give 18 g of di-ketone product (c).

Reaction Step III-1 and IV-1:

Preparation of potassium acetylene reagent: 15 g of KOH solution (20% w/w) was colded to 4° C. in 250 mL three-necked flask and injected with acetylene to stable mass. 6 g of di-ketone product (c) was dissolved in 42 mL of THF and then added in three-necked flask thereto 25° C. for 2 hours. The product was diluted with H₂O and acidified with HCl. The residue was filtrated, washed with H₂O and dried to give 5.9 g of the 2,17α-diethynyl-A-nor-5a-androstane-2,17β-diol product (e).

Reaction Step V:

2.8 g of 2,17α-diethynyl-A-nor-5a-androstane-2,17β-diol product (e), 4.5 mL of propionic acid and 7.8 mL of propionic anhydride were mixed in 100 mL of flask, and then stirred for 3 hours. 30 mL of H₂O and 40 mL of ethyl acetate were added in flask, stirred and separated water and organic phase. Organic phase was washed by water for 5 times and added 10 mL n-hexane. The residue was filtrated and dry to give 2.0 g of mixture of product α-anordrin and β-anordrin (fα and fβ), respectively.

In accordance with some embodiments of the present invention, asymmetic synthesis of α-anordrin can be prepared as described in using steps detailed below method II (as shown in Scheme II).

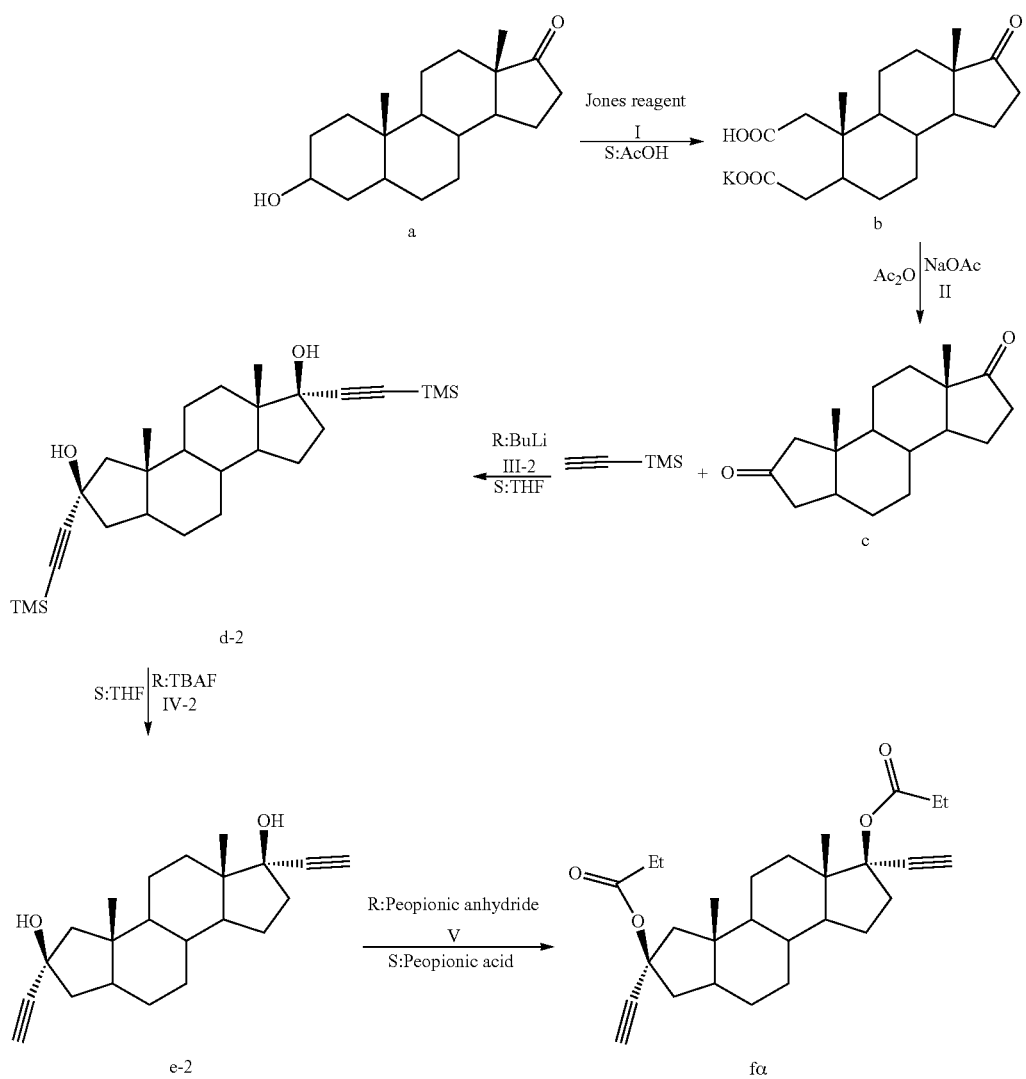

Similar to Method I, di-ketone product (c) was prepared using reaction steps I and II as described above.

Reaction Step III-2:

6 mL of dried THF, 9.2 mL of trimethylsilylacetylane (TMS) were added in a dried 250 mL three-necked flask, and then cooled to −40-−80° C., 20 mL of n-buLi was added in solution and stirred for 30 min, 7 mL of tetramethylehtylenediamine (TEMED). 6 g of di-ketone product (c) from reaction step II of method I was dissolved in 42 mL of THF, and then cooled to −40-−80° C. Mix two solutions together and react for overnight. The reaction was stopped by NH$_4$Cl solution. 100 ml ethyl acetate was added in flask and stirred for 5 min. Organic phase was dried to give 4.8 g of product (d-2).

Reaction Step IV-2:

4.8 g product (d-2) was dissolved in the mixture of 15 ml THF and 17 ml tetrabutyl ammonium fluoride (TBAF) solution to react for 3 hours. THF was distillated. The 2α, 17α-diethynyl-A-nor-5a-androstane-2β,17β-diol product α-anordiol (e-2) was dissolved in ethyl acetate. The organic solution was washed by distilled water for 3 times. After removing ethyl acetate, 3.5 g of 2α, 17α-diethynyl-A-nor-5a-androstane-2 β,17β-diol product, α-anordiol (e-2), was given.

Reaction Step V:

2.8 g of the 2α,17α-diethynyl-A-nor-5a-androstane-2 β,17β-diol product (e-2), 4.5 mL of propionic acid and 7.8 mL of propionic anhydride were mixed in 100 mL of flask, and then stirred for 3 hours. 30 mL of H$_2$O and 40 mL of ethyl acetate were added into flask, stirred and separated water and organic phase. Organic phase was washed by distilled water for 5 times and 10 mL of n-hexane was added. The residue was filtrated and dry to give 2.0 g of mixture of product, α-anordrin (fα).

Figure 1B:
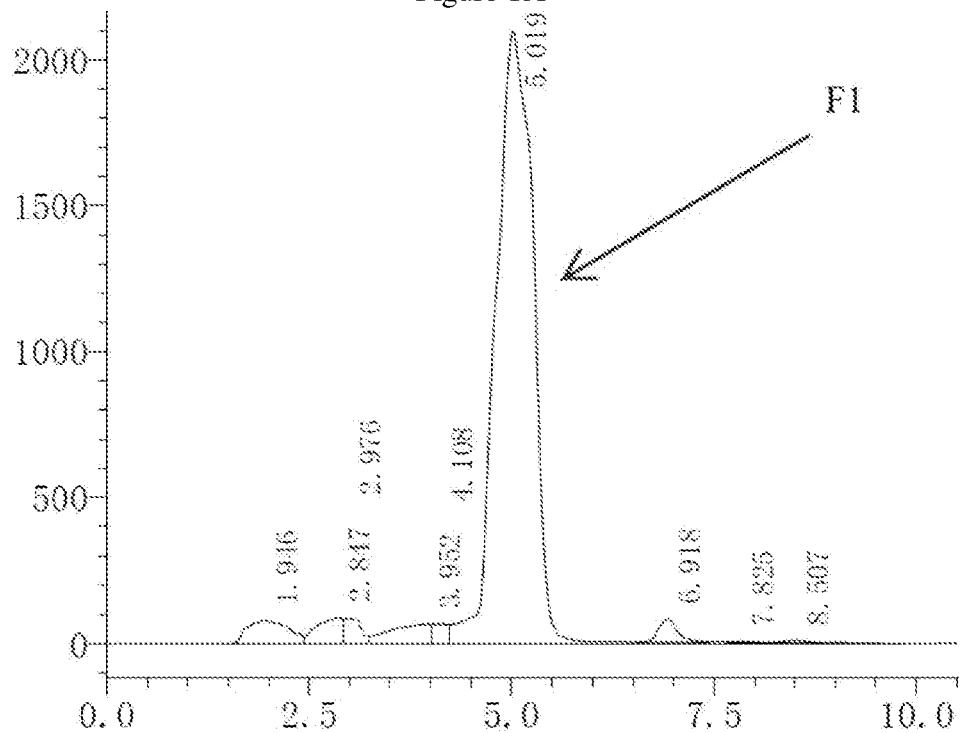
(FIG. 1B) Only α-anordrin (fraction 1 (F1)) in the product of synthesis method II.

The silica gel chromatography analysis showed that only one diastereomeric compound was synthesized using method II (FIG. 1B). In contrast, using method I, the mixture of diastereomeric compounds was synthesized (FIG. 1A).

Figure 2A:
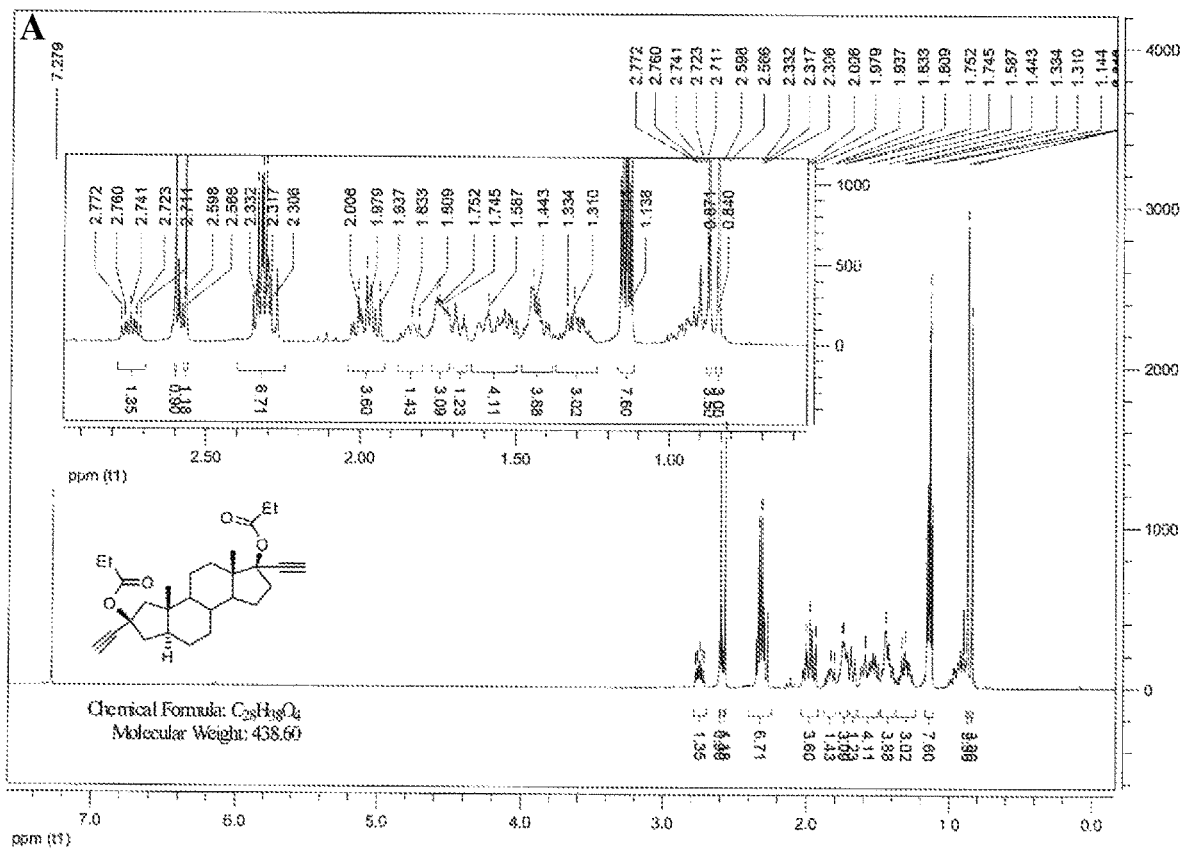
FIG. 2: The NMR analysis of (FIG. 2A) α-anordrin ((2α,17α)-diethynyl-(2β, 17β)-diol-dipropionate-A-nor-5α-androstane) and (FIG. 2B) β-anordrin ((2β,17α)-diethynyl-(2α,17β)-diol-dipropionate-A-nor-5α-androstane).
Figure 2B:
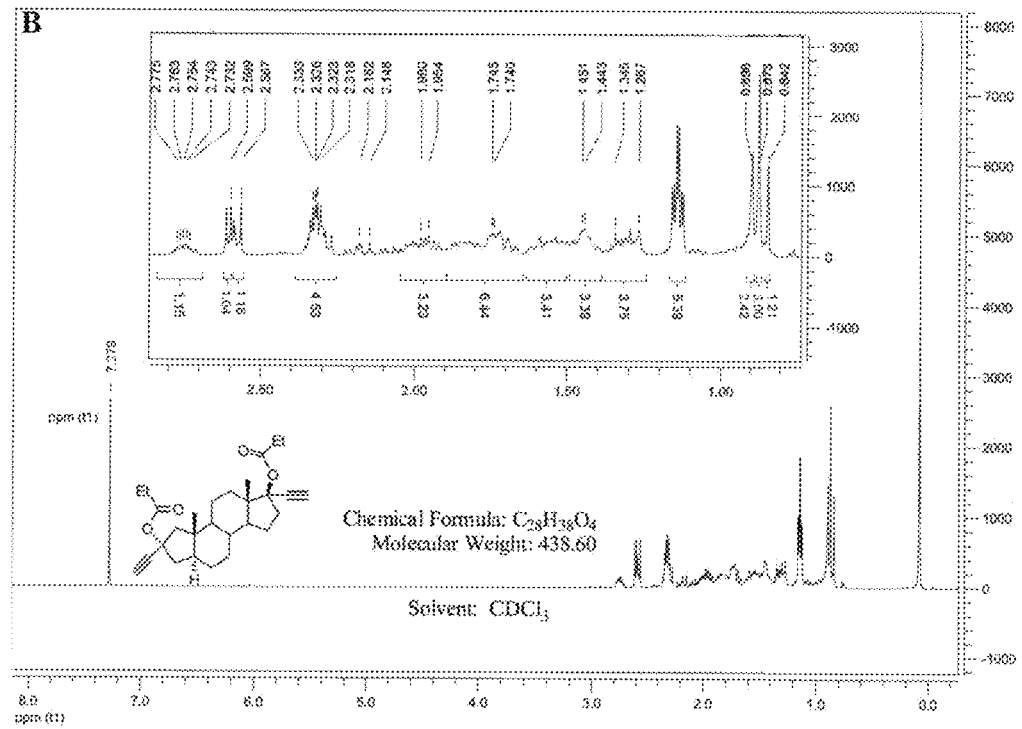
Figure 3A:
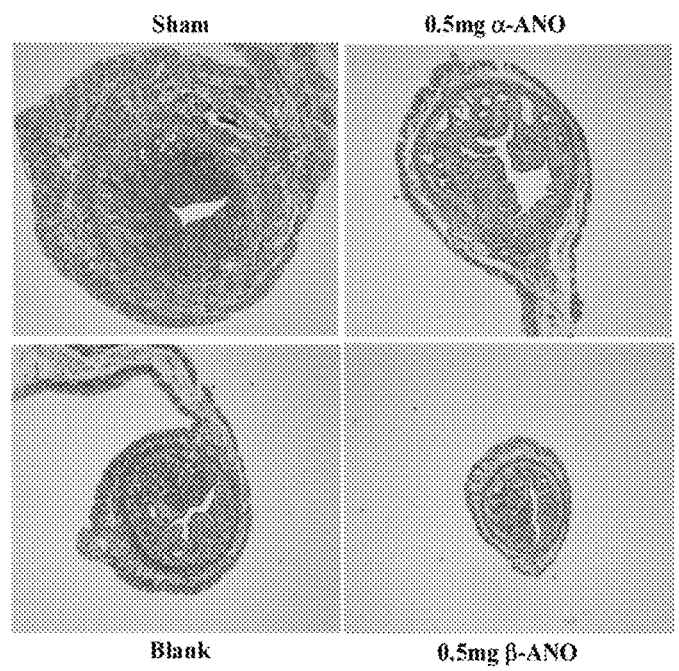
(FIG. 3A) Paraffin-embedded H&E sections (20× magnifications) of mice uterus treated by drugs for three months.
Figure 3B:
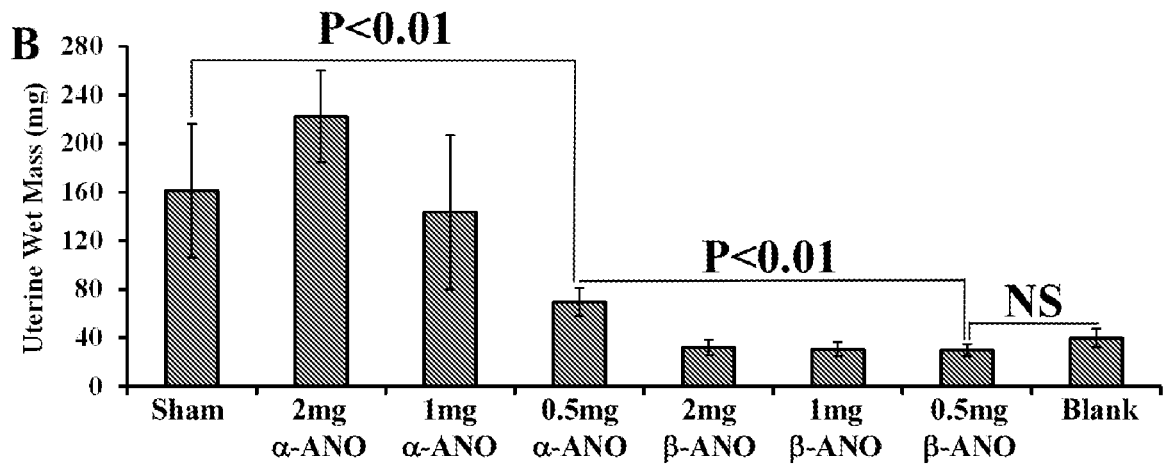
(FIG. 3B) Statistical analysis of mice uterine wet mass, as measured from H&E-stained sections, as in (FIG. 3A). N=12.
Figure 3C:
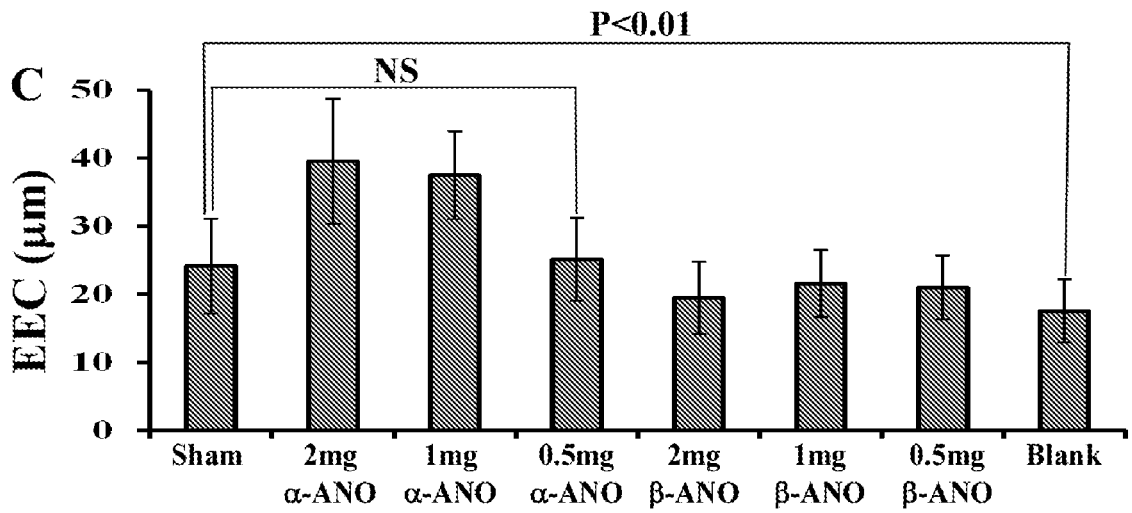
(FIG. 3C, FIG. 3D and FIG. 3E) Statistical analysis of mice uterine height of EEC (μm) (shown in FIG. 3C), diameter (mm) (shown in FIG. 3D) and the thickness of circular muscle (μm) (shown in FIG. 3E), respectively, as measured from H&E-stained sections, as in (FIG. 3A). N=12.
Figure 3D:
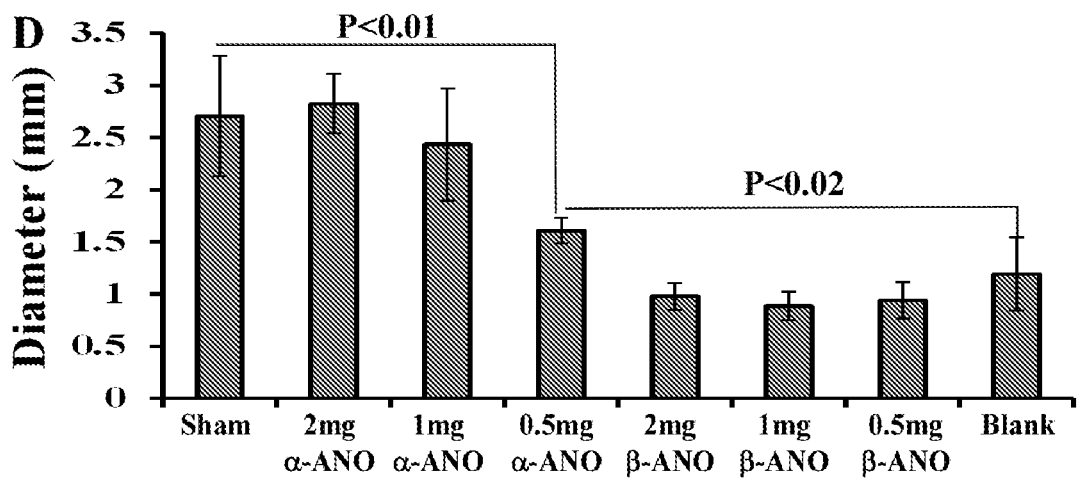
Figure 3E:
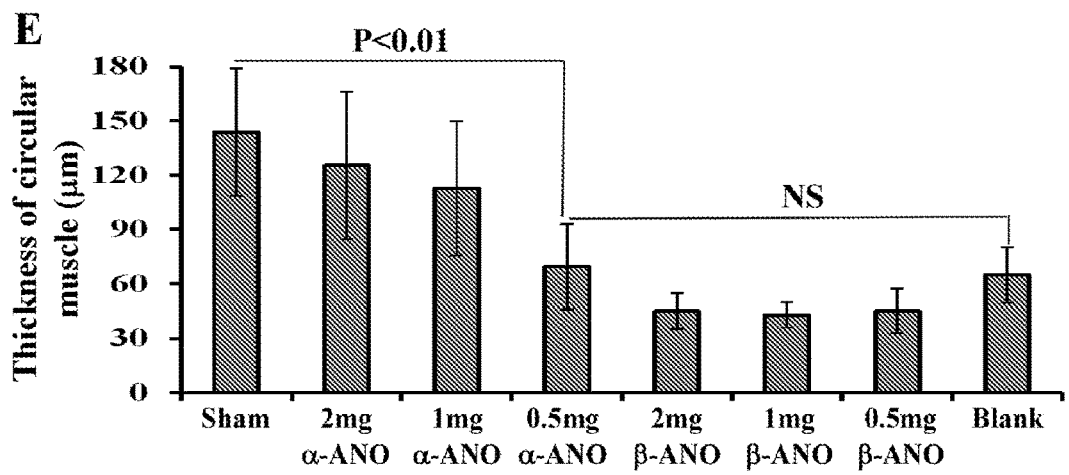

NMR analysis: Collecting fraction 1 (F1) and fraction 2 (F2) and dissolving in CCl$_4$ (50 mg/mL) for NMR analysis. FIG. 2A and FIG. 2B showed α-anordrin from fraction 1 (F1) and β-anordrin from fraction 2 (F2), respectively.

Example 2: Effects of α-Anordrin or β-Anordrin

In this Example, studies have been shown the estrogenic effects of α- and β-anordrins on estrogen-modulated metabolic signaling and tissue atrophy. The ovaries of 7 week old mice were surgically excised. One week post surgery, the mice were given isoflavone, α-anordrin or β-anordrin by food. Body mass, blood glucose and food intake were measured monthly. After three months. Mice were sacrificed. The leg and spine bone, liver, uterus and vagina were harvested.

Figure 4A:
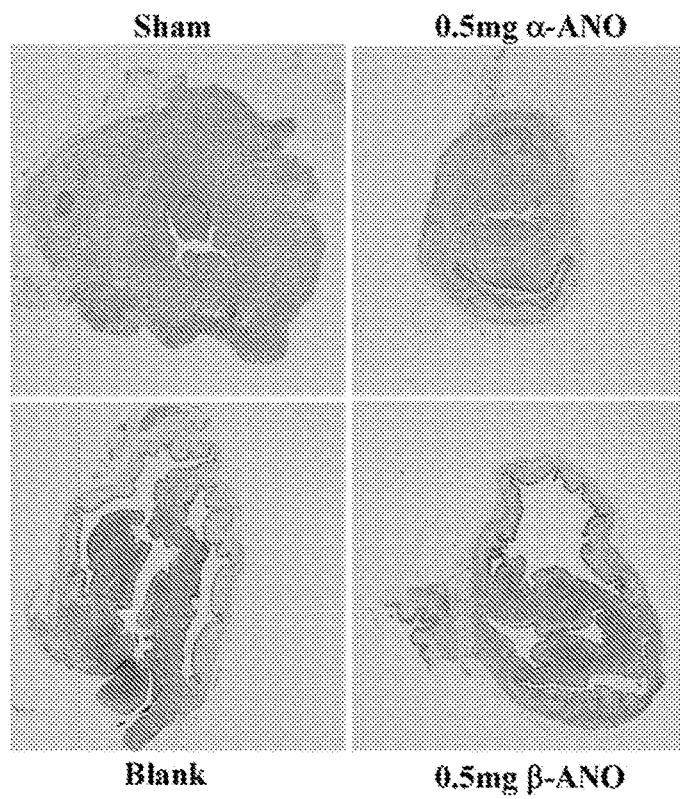
(FIG. 4A) Paraffin-embedded H&E sections (20× magnifications) of mice vagina treated by drugs for three months.
Figure 4B:
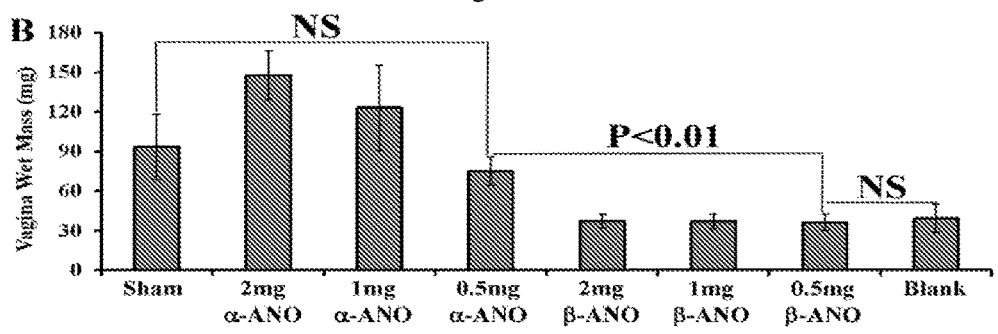
(FIG. 4B and FIG. 4C) Statistical analysis of mice vagina wet mass (mg) (shown in FIG. 4B) and the thickness of vulvovagina wall (μm) (shown in FIG. 4C), respectively, as measured from H&E-stained sections, respectively, as in (FIG. 4A). N=12.
Figure 4C:
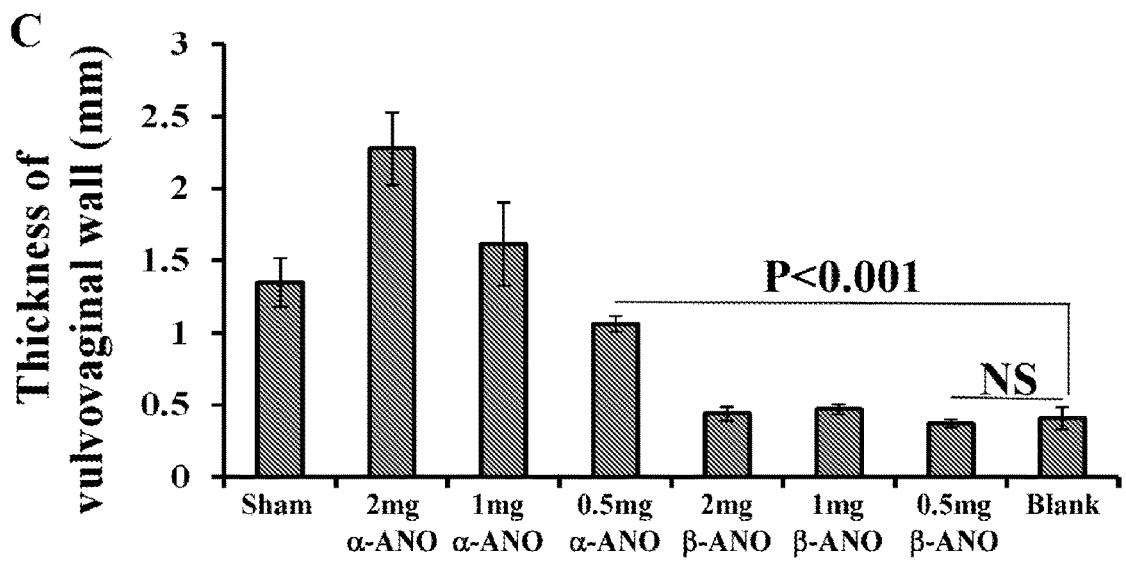
Figure 5A:
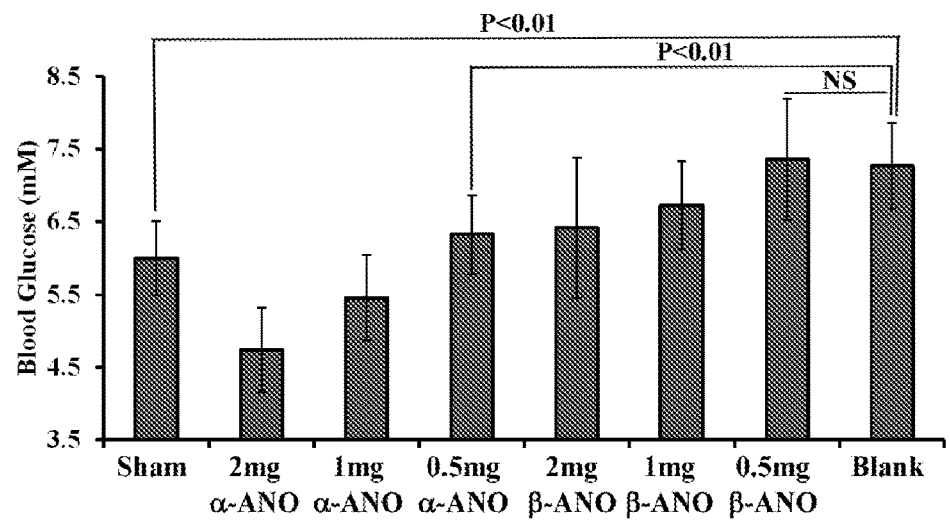
(FIG. 5A) Statistically analyzing the amount of blood glucose (top panel) and triglyceride (TG) (low panel). N=12.
Figure 5A:
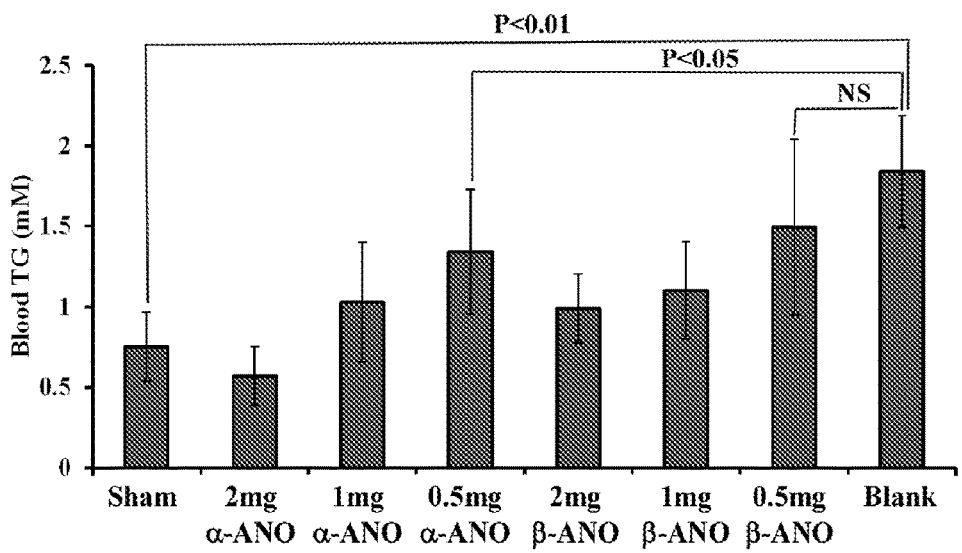
Figure 5B:
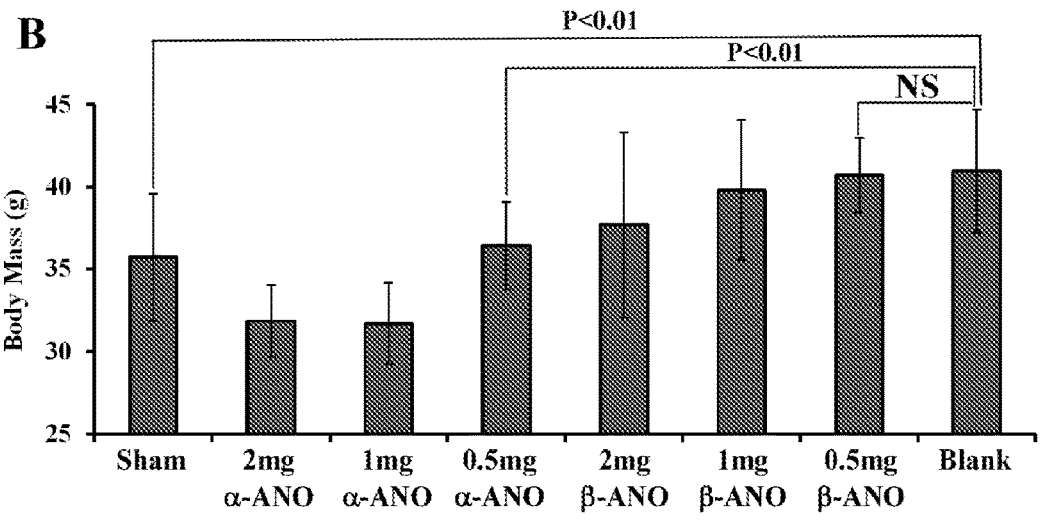
(FIG. 5B) Statistically analyzing the mice body mass (g) after administrated by drugs. N=12.
Figure 5C:
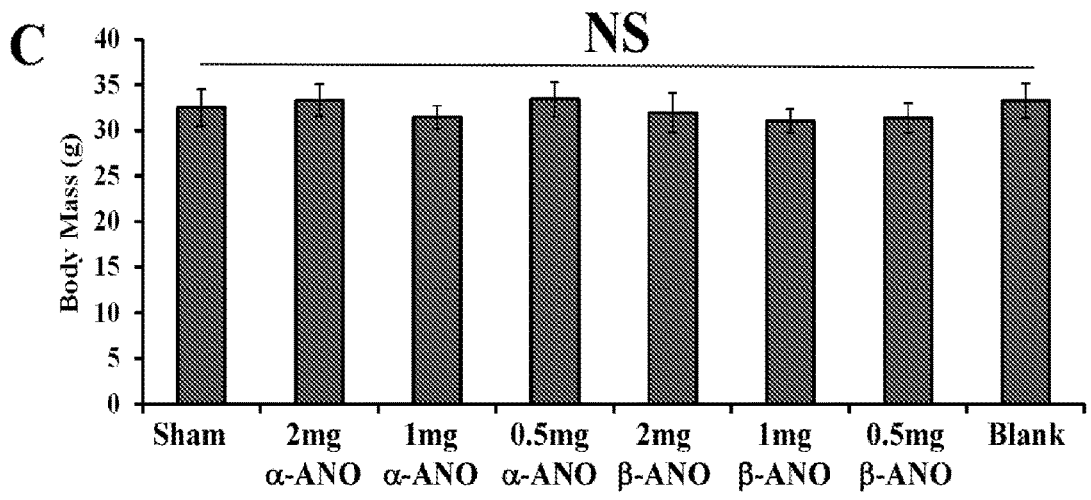
(FIG. 5C) Statistically analyzing the initiated mice body mass (g). N=12. NS means Non-Significantly different.
Figure 5D:
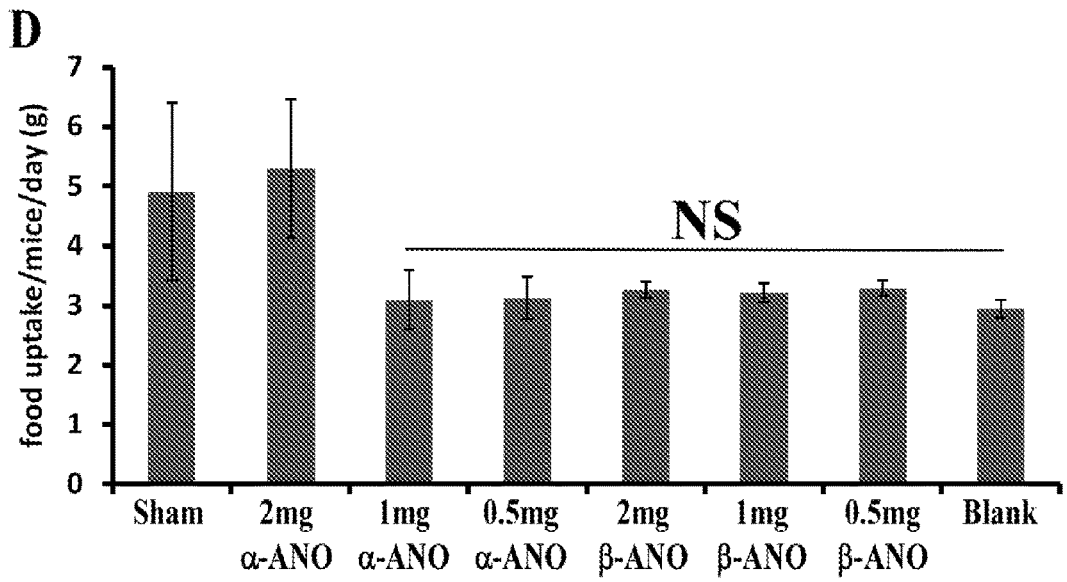
(FIG. 5D) The food uptake by mice daily. N=12. NS means Non-Significantly different.
Figure 6:
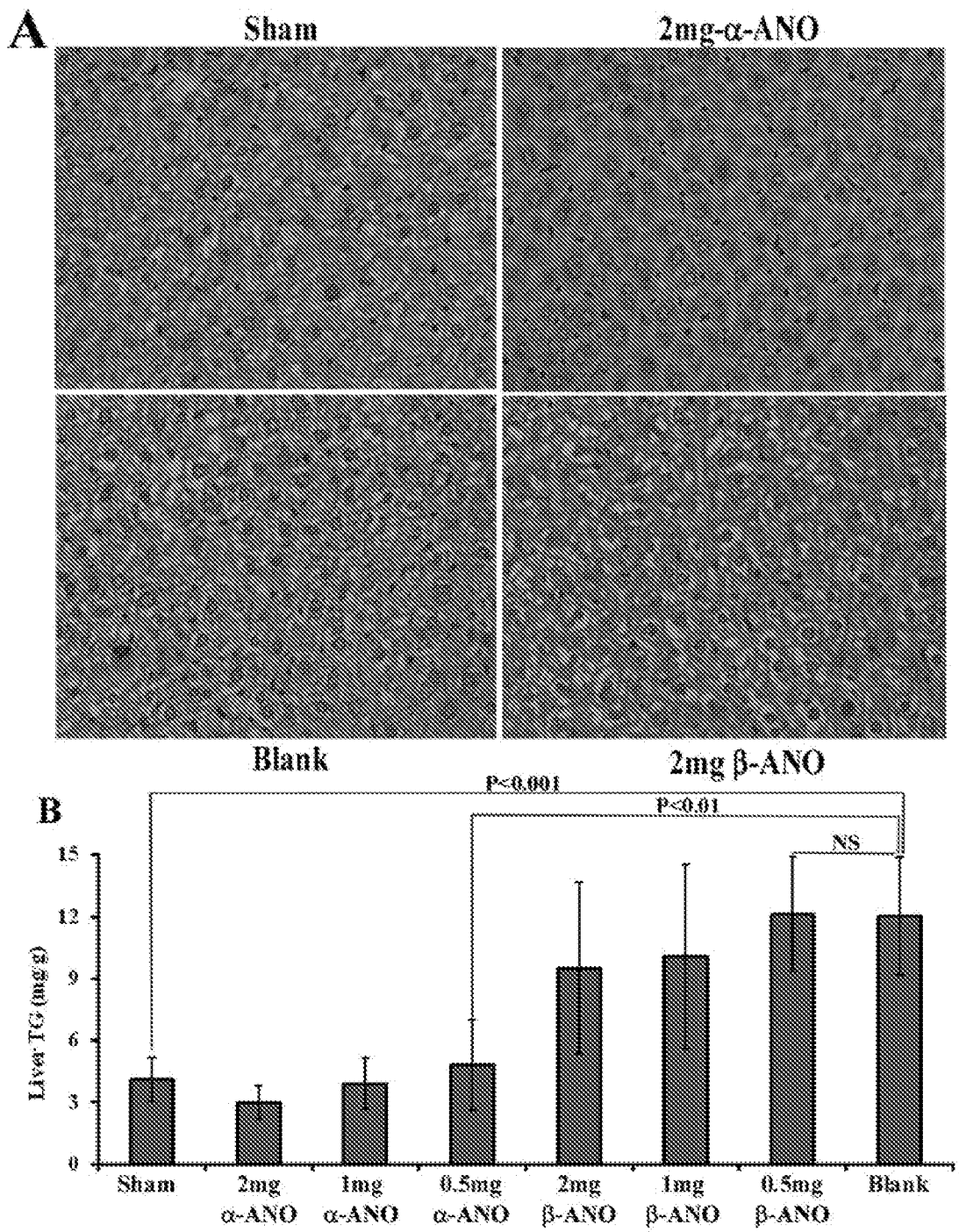
FIG. 6: The α-anordrin (α-ANO) shows dosage dependent activity to prevent TG accumulation in liver compared with β-anordrin (β-ANO) in OVX female mice.
Figure 7A:
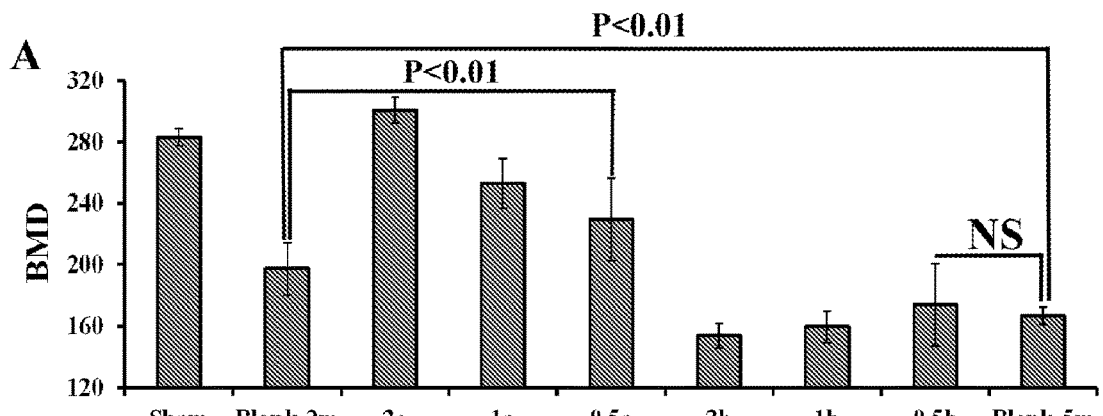
(FIG. 7A) The α-anordrin show more activity to prevent the loss of bone mean density (BMD) compared with β-anordrin in OVX female mice. N=12.
Figure 7B:
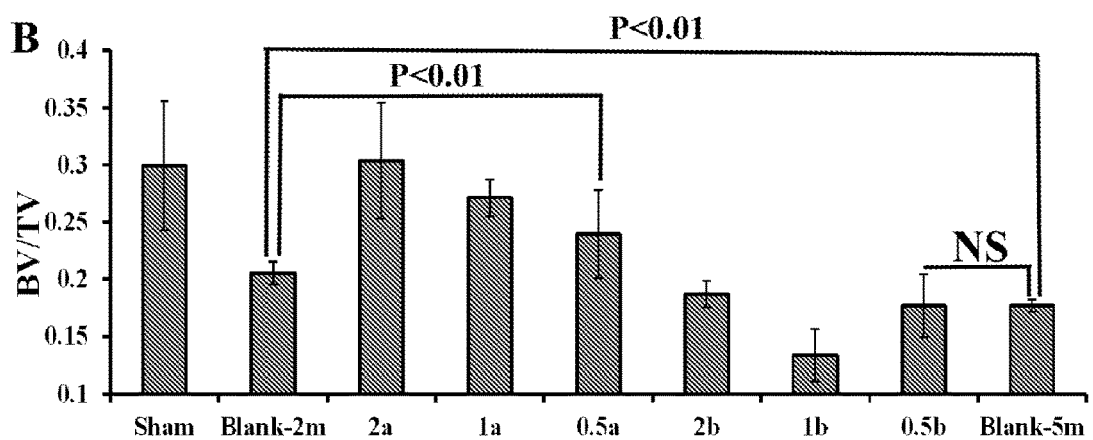
(FIG. 7B) The α-anordrin show more activity to prevent the ratio decreasing of bone volume (BV)/bone trabecula volume (TV) (BV/TV) compared with β-anordrin in OVX female mice. N=12.

The uterus and vagina wet mass and H&E staining showed that α-anordrin but not β-anordrin prevented vulvovagina atrophy (FIG. 4). The α-anordrin-treated OVX mice showed less atrophy symptom in uterus compared with those mice treated by β-anordrin and blank groups (FIG. 3). The α-anordrin showed the less blood glucose, TG and body mass compared with 3-anordrin (FIG. 5A and FIG. 5B), respectively, but initiation body mass and food uptake was not significantly different (FIG. 5C and FIG. 5D), respectively. These data indicated that the differences were due to changes in energy expenditure. The liver H&E section and statistical analysis showed that α-anordrin but not β-anordrin decreased the amount of liver TG in OVX mice (FIG. 6). The micro-CT result shows that α-anordrin but not 3-anordrin prevented osteoporosis in OVX mice (FIG. 7).

Tamoxifen was the first FDA-approved drug for breast cancer patients with positively expressed ER. However, tamoxifen also induces side effects, such as uterine endometrial cancer and NASH. Importantly, for women with ER-positive (ER$^+$) cancer, continuing tamoxifen treatment for up to 10 years, rather than stopping at 5 years, produces further reductions in recurrence and mortality, particularly after year 10. We found that anordrin can eliminate tamoxifen-induced endometrial epithelial cell (EEC) mitosis. We further tested whether α-anordrin or β-anordrin eliminates tamoxifen-induced EEC mitosis. The 7 week old mice were given by food containing isoflavone (Blank), α-anordrin (α-ANO), β-anordrin (b-ANO), α-anordrin+tamoxifen (TAM+α-ANO), β-anordrin+tamoxifen (TAM+b-ANO) or tamoxifen (TAM) for 6 months. Mice were then sacrificed to harvest uterus and liver. Uterine and liver tissues were fixed.

Figure 8A:
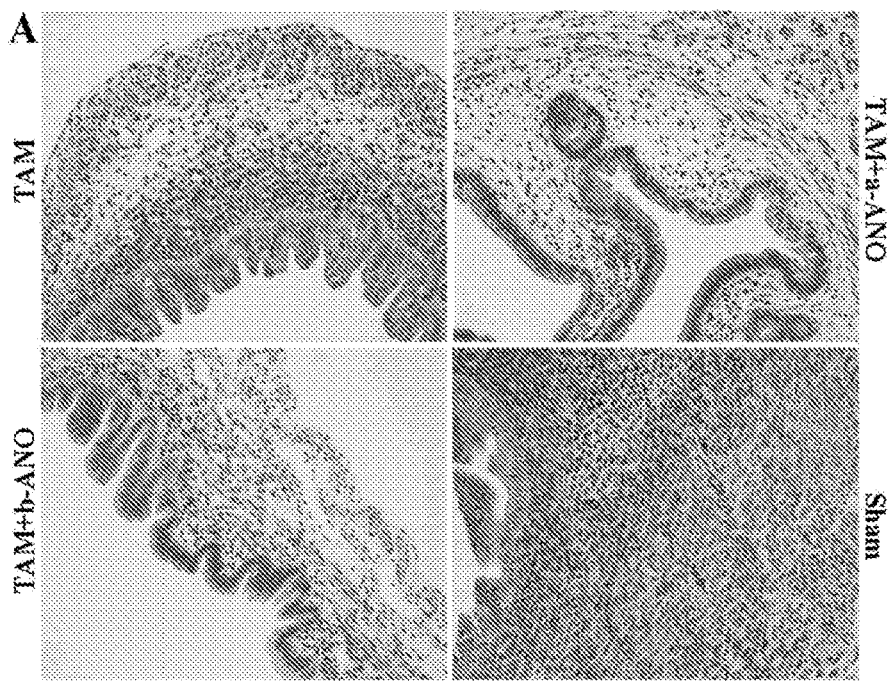
(FIG. 8A) Paraffin-embedded H&E sections (200× magnifications) of EECs from mice uterus treated by drugs for 6 months.
Figure 8B:
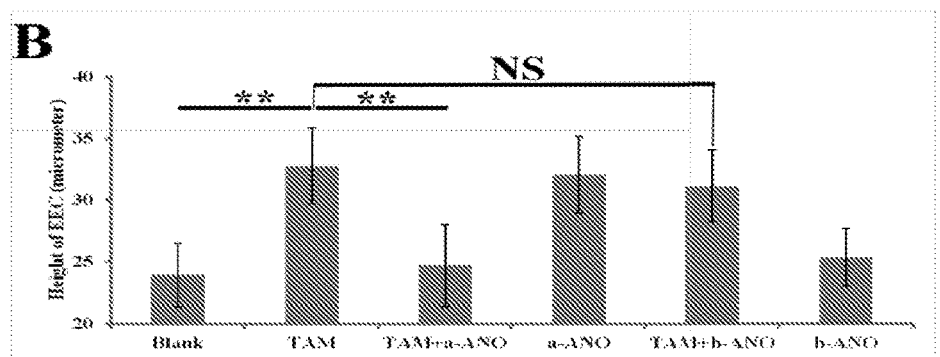
(FIG. 8B) Statistical analysis of the EEC height (μm), as measured from H&E-stained sections, as in (A). N=6. ** means P<0.01.
Figure 9:
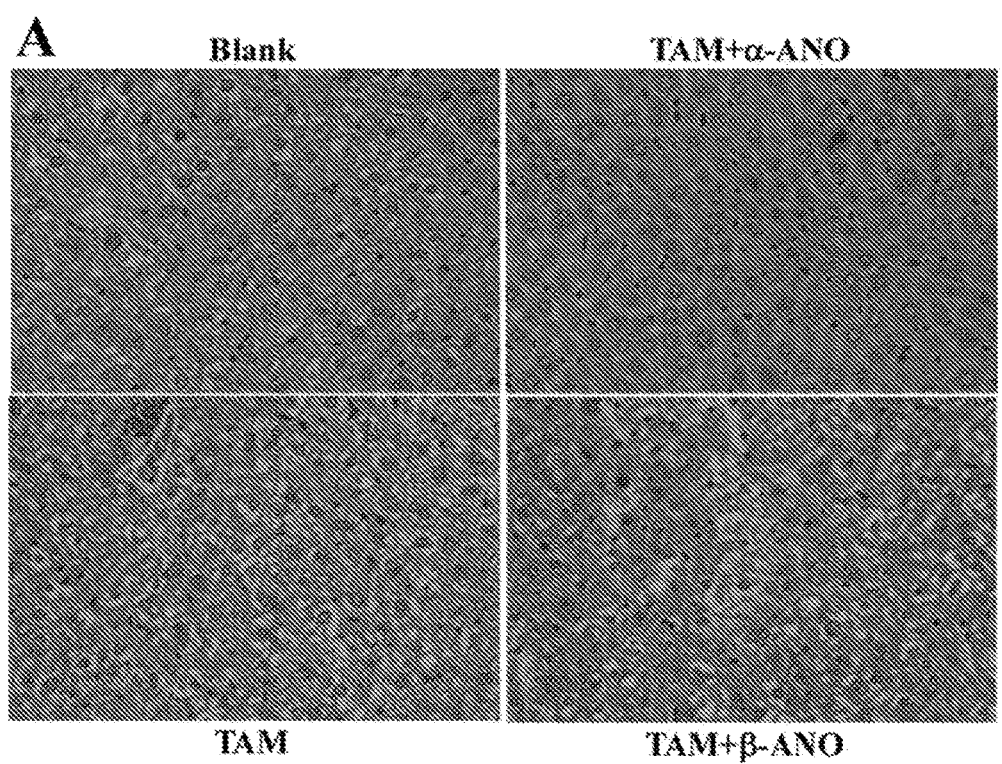
FIG. 9: The α-anordrin inhibits tamoxifen-induced NASH. TAM or α-ANO or b-ANO: mice were treated with tamoxifen (TAM) or α-anordrin (α-ANO) or β-anordrin (b-ANO) alone. TAM+α-ANO or TAM+b-ANO mice were treated with the combination of tamoxifen and α-anordrin or β-anordrin, respectively. Blank mice were treated by vehicle.
Figure 9:
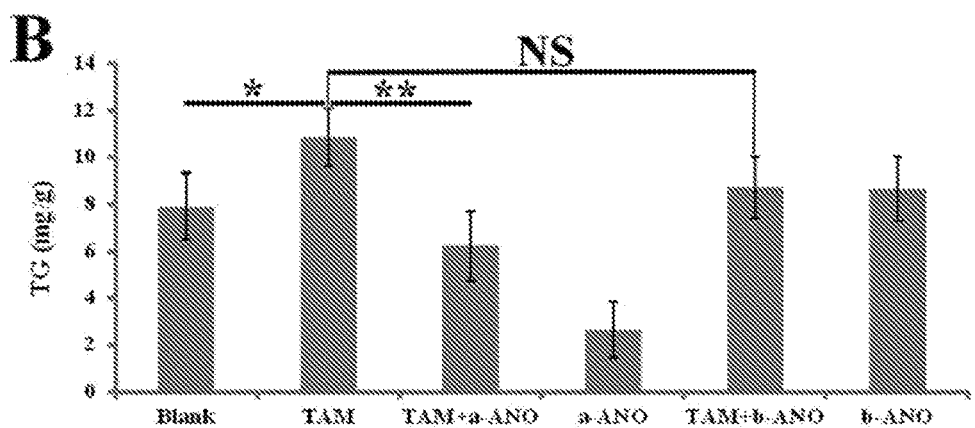

H&E staining sections showed that EECs in TAM+b-ANO and TAM groups are rough and mitotic compared with smooth and single layer EEC in TAM+α-ANO and sham groups (FIG. 8A), and the high fatty deposition in liver cells of TAM+b-ANO and TAM groups compared with those liver cells in TAM+α-ANO and sham groups (FIG. 9A). The statistical analysis of H&E staining sections showed that α-anordrin but not β-anordrin inhibited tamoxifen-induced EEC mitosis (FIG. 8B) and NASH (FIG. 9B).

Figure 10A:
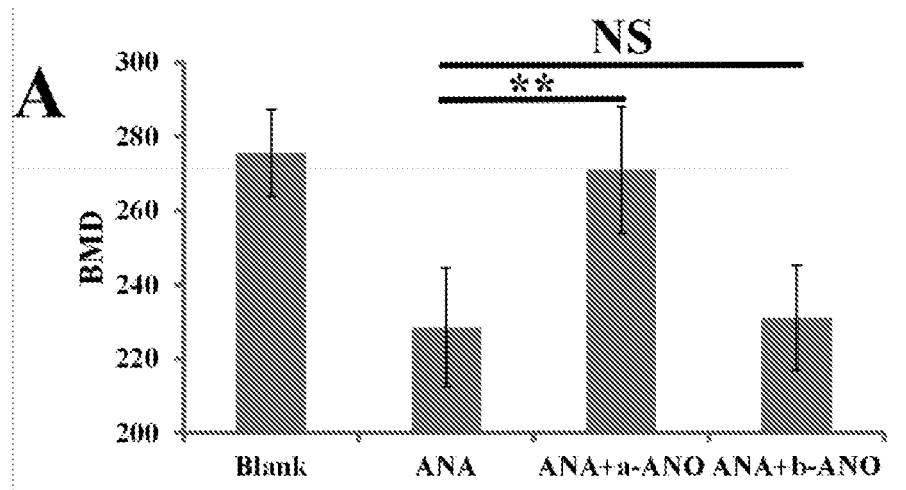
(FIG. 10A) The α-anordrin inhibits anastrozole-induced the loss of bone mean density (BMD). N=6.  indicates P<0.01.
Figure 10B:
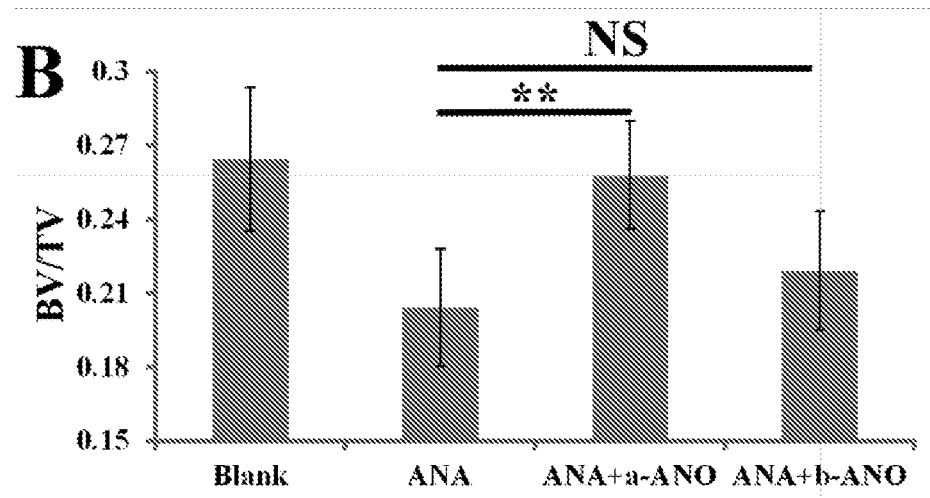
(FIG. 10B) The α-anordrin inhibits anastrozole-induced the ratio decreasing of bone volume (BV)/bone trabecular volume (TV) (BV/TV). N=6.  indicates P<0.01.
Figure 10C:
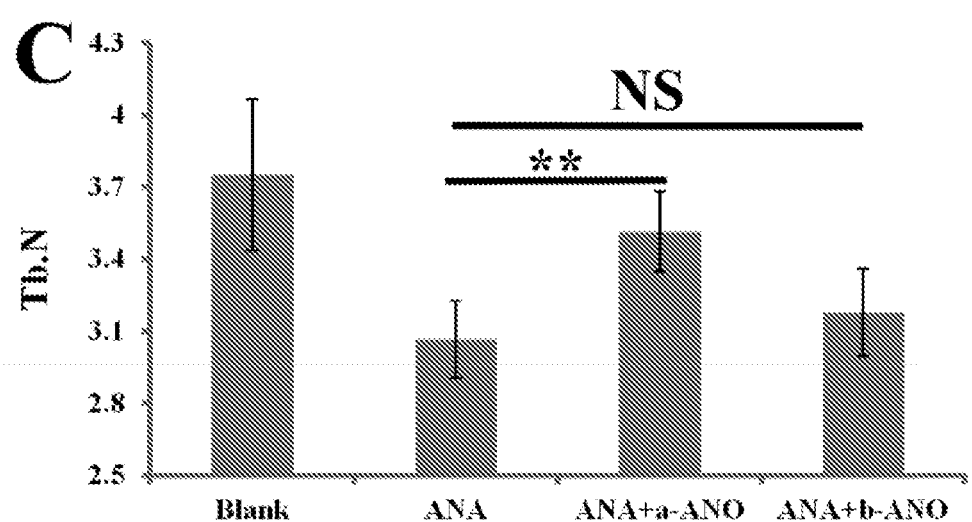
(FIG. 10C) The α-anordrin inhibits anastrozole-induced the decreasing of bone trabecula number (Tb.N) N=6. ** indicates P<0.01.
Figure 11A:
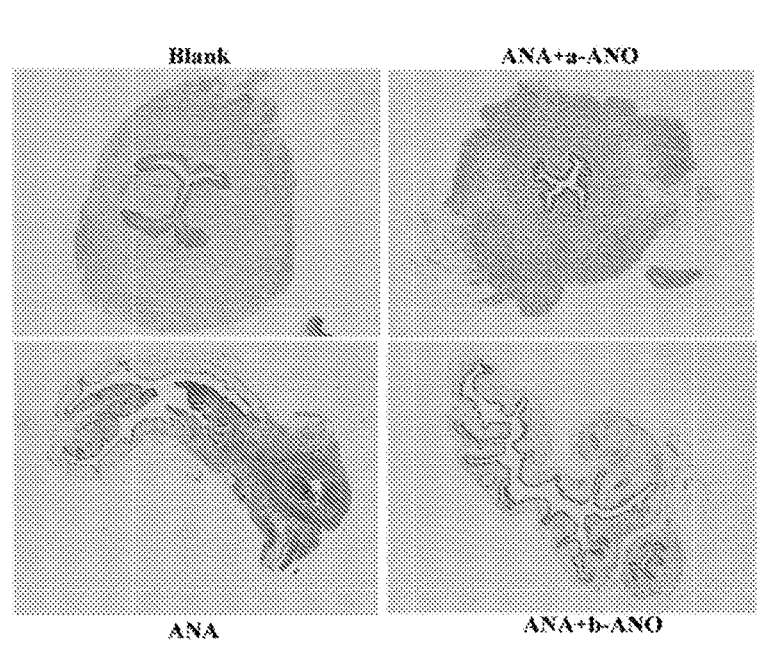
(FIG. 11A) Paraffin-embedded H&E sections (40× magnifications) of normal mouse vagina treated by drugs.
Figure 11B:
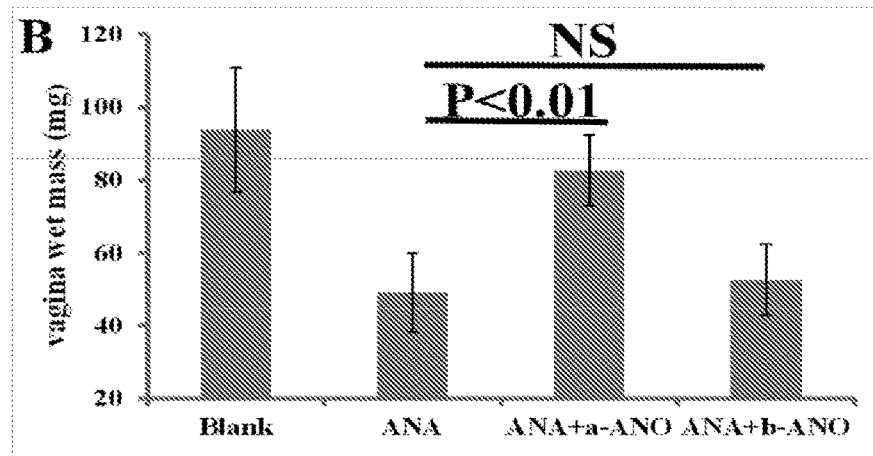
(FIG. 11B and FIG. 11C) Statistical analysis of vulvovaginal wet mass (mg) (shown in FIG. 11B) and the thickness of circular muscle (μm) (shown in FIG. 11C), respectively, as in (FIG. 11A); N=6.
Figure 11C:
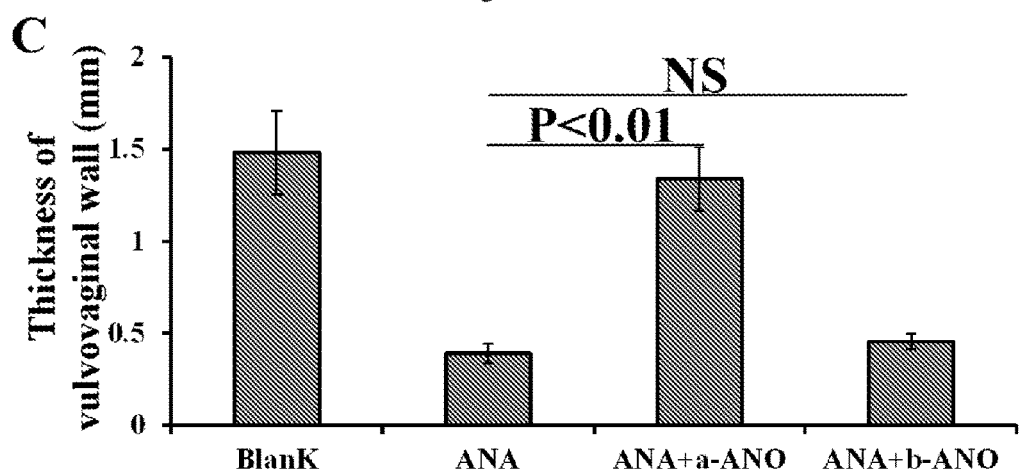

Aromatase inhibitors were administrated to ER positive breast in post-menopausal women. It also induced side effects such as tissue atrophy and osteoporosis et al. Anastrozole is an aromatase inhibitor. It was administrated to ER positive breast cancer in post menopausal women. Anastrozole (ANA) also induced vagina atrophy and osteoporosis. Vulvovagina atrophy usually results in infection of vagina and urinary tract. As an example, we tested whether α-anordrin or β-anordrin eliminates anastrozole-induced uterus and vulvovagina atrophy, and osteoporosis. The 7 week old mice were given by food containing isoflavone (Blank), α-anordrin (α-ANO), β-anordrin (b-ANO), α-anordrin+anastrozole (ANA+α-ANO), β-anordrin+anastrozole (ANA+b-ANO) or anastrozole (ANA) for 6 months. Mice were then sacrificed to harvest vagina, leg and spine bone. The tissues were fixed in paraformaldehyde. Micro-CT results showed that α-anordrin but not β-anordrin inhibited anastrozole-induced osteoporosis (FIG. 10 A, FIG. 10B and FIG. 10C). The statistical analysis of vagina wet mass and H&E staining sections of vulvovagina showed that that α-anordrin but not β-anordrin inhibited anastrozole-induced vagina atrophy (FIG. 11A, FIG. 11B and FIG. 11C).

Example 3: Materials and Material Preparation Methods

Tamoxifen and anastrozole (MPG USP GRADE) were offered by Okahata (Shanghai) Trading Co., Ltd. Epiandrostenestone was purchase from Jiangsu Jiaerke Pharmaceuticals Group, LTD. All other compounds were purchased from Sigma or Aladdin. Mice food was made by Trophic Animal Feed High-tech Co., Ltd, Nantong, China. Mice were purchased from BK animal Inc. The animal experiment was performed in the Southern Center of Pesticide Research, Shanghai.

Glucose Concentration Assay:

glucose concentration in medium or total blood from mouse tail was measured using glucose assay kits following manufacturer's instructions (Yicheng, Beijing).

Construction of Ovariectomized (OVX) Mice Model and Administration of Drugs:

The ovaries of 6 week old mice were excised by surgery. 3 days post surgery drugs were administered by gastric tract injection every day or mixed with food.

Preparation of Paraffin Sections and HE Staining:

The tissue of mice was excised by surgery and fixed using 4% paraformaldehyde in 1×DPBS (Beijing Solar Bioscience & Technology co., Ltd). Paraffin section preparation and HE staining was performed by GLP laboratory of BK animal model, Inc.

Measurement of TG in Mice Liver:

30-50 mg of mouse liver was excised by surgery and homogenized in 1 ml Cholroform:Methanol (2:1) mixture and extracted using 0.5 ml ddH$_2$O. The organic phase was transferred to new tubes and air dried. The amount of TG was measured using kits following manufacturer's instructions. The error was corrected by using internal standard controls.

Measurement of the EEC Height, Uterine Diameter and Circular Muscle Thickness:

EEC height was measured from 20-200× magnification EEC images of Paraffin-embedded H&E mice uterus sections.

Measurement of the Thickness of Vulvovaginal Wall:

Vagina was cut at the middle site. Both uterine site and vulvovaginal site were embedded in paraffin at the same direction for H&E section preparation. The thickness of vulvovaginal wall was measured from 40× magnification images of Paraffin-embedded H&E mice vagina sections.

Bone Density Assay Using Micro-CT:

Thighbone was fixed in 1×DPBS containing 3% formaldehyde for two weeks. The fixation solution was exchanged after one week. The density of thighbone was measured by Siemens Inveon Micro-CT. Inveon Research Workplace (IRW) was used to analyze the HU2000 value at the following measurement conditions: 80 KVP, 500 mA, 1500 ms exposure time; CCD Readout installation: 2048axial, 2048 binning; FOV Transaxial: 19.03 mm, axial: 19.03 mm, pixels size: 9.29 μm.

Statistical Analysis:

In tables and figures, the results were presented as mean+ STDEV. Asterisks indicate a statistically significant difference calculated using student's t-test, two-tailed.

REFERENCES

1. Boonyaratanakornkit, V., Steriods. 76, 877-884, (2011).
2. Mauvais-jarvis, F., Clegg, D J., and Hevener, A I., Endocrine Reviews. 34(3), 309-338 (2013)
3. Kuang, L G., Zhang, X T., Xie, Y., et al., Molecular endocrinology. 24(4), 709-721 (2010)
4. Rao, J., Jiang, X M., Wang, Y., and Chen, B., Journal of Steroid Biochemistry and Molecular Biology. 127, 231-237 (2011)
5. Revankar, C M., Cimno D., Sklar, L A., Arterburn, J B., and Prossnitz, E R. Science. 307 (11), 1625-1630 (2005)
6. Nilsson, B O., Olde, B., and Leeb-Lundberg, L F. British Journal of Pharmacology. 163. 1131-1139 (2011)
7. Zhang, X T., Ding, L., Kang, L G., and Wang, Y., PLos one. 7(1), e30174 (2012)
8. O'Brien, J E., Peterson, T J., Tong, M H., et al. J. of Biol. Chem. 281(36). 26683-26692 (2006)
9. Takamura, T., shimizu, A., Kumura, T., Ando, K Zen, Y., et al. Internal Med. 579-581 (2007)
10. Barrett-Connor, E., Mosca, L., Collins, P., et al., N Engl. J. Med., 355. 125-137 (2006)
11. Alexanderson, P., Toussaint, A., Christiansen, C., et al., JAMA. 285(11). 1482-8 (2001)
12. Hershberger, P A., Stabile, L P., Kanterewicz, B., et al., J. of Steroid Biochem. & Mol. Biol. 16. 102-9 (2009)
13. Bank, U. K. and Pincus, U., Proc. Soc. Expt. Biol. Med. 111, 595 (1962).
14. Pincus, U. and Gordon, H. L., Steroids, 5, 193, (1965).
15. Xu, B., Zhou, P. Q., and Yu, W. J., Tumor, 9, 197 (1989).
16. Ma, Z. C., Lou, L. G., Zhang, Z., and Bin, X, Acta Pharmacol. Sin, 21, 939 (2000).
17. Li R. L., Lee, D. Y., Cheng, Q. L., U.S. Pat. No. 5,001,120 (1991).
18. Mehta, R. R., Jenco, J. M., and Chatterton, R. T., Steroids, 38, 679 (1981).
19. Li Z H, Li L. X-ray diffraction studies on the absolute configuration of alpha- and beta-anordrins. Steroids. 1990 December; 55(12):565-70.
20. Nehra, R., Riggins, R B., Shajahan, A N et al., FASEB J. 24(6). 2040-55 (2010).
21. Gu W, Xu W, Sun X, Zeng B, Wang S, Dong N, Zhang X, Chen C, Yang L, Chen G, Xin A, Ni Z, Wang J, Yang J. Anordrin Eliminates Tamoxifen Side Effects without Changing Its Antitumor Activity. Sci Rep. 2017 Mar. 7; 7:43940.

What is claimed is:

1. A method for stereospecifically preparing a substantially pure diastereomeric compound of formula (I):

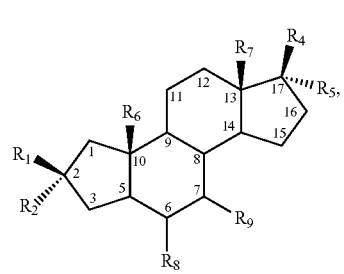

or a salt thereof,
wherein the substantially pure diastereomeric compound has a diastereomeric excess (de) of no less than 99%, wherein
$R_1$ is —OH, —OC(O)—$R^{1a}$ or —OC(O)$R^{1b}$COOH and $R^4$ is —OH, —OC(O)—$R^{4a}$ or —OC(O)$R^{4b}$COOH, wherein $R^{1a}$ and $R^{4a}$ are independently hydrogen, $C_1$-$C_6$alkyl, $C_2$-$C_6$alkenyl, $C_2$-$C_6$ alkynyl or $C_3$-$C_6$ cycloalkyl, and $R^{1b}$ and $R^{4b}$ are independently-$C_1$-$C_6$alkyl- or —$C_2$-$C_6$alkenyl-;
$R_2$ and $R_5$ are —C≡CH;
$R_6$ and $R_7$ are independently $C_1$-$C_6$alkyl, $C_2$-$C_6$alkenyl, $C_2$-$C_6$ alkynyl or $C_3$-$C_6$ cycloalkyl;
$R_8$ and $R_9$ are independently hydrogen, —OH, —$NH_2$, —$NO_2$, halogen, $C_1$-$C_6$alkyl, $C_2$-$C_6$alkenyl, $C_2$-$C_6$ alkynyl, $C_3$-$C_6$ cycloalkyl, $C_6$-$C_{14}$ aryl, 5-6-membered heteroaryl or 3-6 membered heterocyclyl,
comprising:
(a) reacting a di-ketone compound of formula (II)

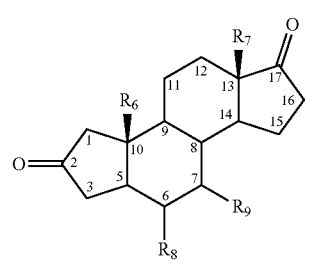

with a silylacetylene of formula (III)

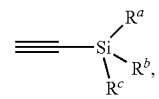

wherein $R^a$, $R^b$ and $R^c$ are independently selected from the group consisting of $C_1$-$C_{20}$ alkyl optionally substituted by —OH, halogen or $C_1$-$C_6$alkyl, $C_1$-$C_6$alkoxy optionally substituted by —OH, halogen or $C_1$-$C_6$ alkyl, $C_3$-$C_6$ cycloalkyl, $C_6$-$C_{14}$ aryl, 5-6-membered heteroaryl or 3-6 membered heterocyclyl,
in the presence of an organometallic reagent $R_{10}$-M, wherein M is Li, Na or K, and $R_{10}$ is $C_1$-$C_{20}$alkyl, optionally substituted by —OH, halogen or $C_1$-$C_6$alkyl,
to form an intermediate of the structure

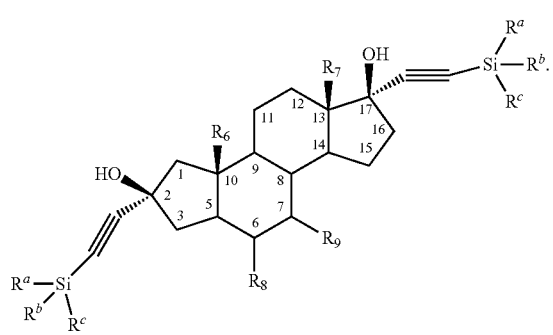

2. The method of claim 1, wherein
R$_1$ is —OH, —OC(O)—R$^{1a}$ or —OC(O)R$^{1b}$COOH and R$_4$ is —OH, —OC(O)—R$^{4a}$ or —OC(O)R$^{4b}$COOH, wherein R$^{1a}$ and R$^{4a}$ are independently hydrogen, C$_1$-C$_6$alkyl, or C$_2$-C$_6$alkenyl, and R$^{1b}$ and R$^{4b}$ are independently —C$_1$-C$_6$alkyl- or —C$_2$-C$_6$alkenyl-;
R$_6$ and R$_7$ are independently C$_1$-C$_6$alkyl or C$_2$-C$_6$alkenyl;
R$_8$ and R$_9$ are independently hydrogen, —OH, —NH$_2$, —NO$_2$, C$_1$-C$_6$alkyl or C$_2$-C$_6$alkenyl.

3. The method of claim 1, wherein R$_1$ is —OC(O)—R$^{1a}$, R$_4$ is —OC(O)—R$^{4a}$, and both R$^{1a}$ and R$^{4a}$ are ethyl.

4. The method of claim 1, wherein both R$_1$ and R$_4$ are —OH.

5. The method of claim 1, wherein R$_1$ is —OC(O)R$^{1b}$COOH, R$_4$ is —OC(O)R$^{4b}$COOH, and R$^{1b}$ and R$^{4b}$ are independently selected from —CH$_2$—, —CH$_2$—CH$_2$— and —CH=CH—.

6. The method of claim 1, wherein both R$_6$ and R$_7$ are methyl.

7. The method of claim 1, wherein R$_8$ and R$_9$ are independently hydrogen or C$_1$-C$_6$alkyl.

8. The method of claim 1, wherein both R$_8$ and R$_9$ are hydrogen.

9. The method of claim 1, wherein R$^a$, R$^b$ and R$^c$ are independently C$_1$-C$_6$alkyl.

10. The method of claim 1, wherein R$^a$, R$^b$ and Re are methyl and the silylacetylene is trimethylsilylacetylene.

11. The method of claim 1, wherein R$_{10}$ is C$_1$-C$_6$alkyl.

12. The method of claim 1, wherein R$_{10}$ is n-butyl.

13. The method of claim 1, wherein M is Li.

14. The method of claim 1, wherein tetramethylethylenediamine (TEMED) is added with the organometallic reagent.

15. The method of claim 1, further comprising (b) removing from the intermediate the silyl groups of formula (IV)

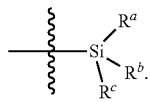
(IV)

16. The method of claim 15, wherein the silyl groups are trimethylsilyl.

17. The method of claim 15, wherein the removing step is carried out by contacting the intermediate with a deprotective agent selected from the group consisting of tetrabutyl ammonium fluoride (TBAF), hydrofluoric acid and potassium fluoride.

18. The method of claim 1, wherein the substantially pure diastereomeric compound is (2α,17α)-diethynyl-(2β, 17β)-diol-dipropionate-A-nor-5α-androstane (α-anordrin) of formula (Ia)

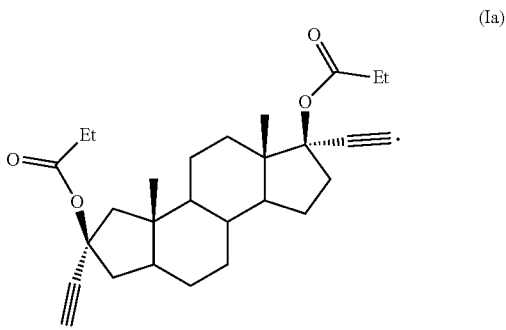 [SMILES: C#C[C@@]1(OC(=O)CC)CC2CCC3C(CC[C@@]4(C)C3CC[C@]4(C#C)OC(=O)CC)[C@@]2(C)C1]
(Ia)

19. The method of claim 1, wherein the substantially pure diastereomeric compound has a diastereomeric excess (de) of no less than 99.5%.

20. The method of claim 1, wherein the method is carried out at a temperature between about −40° C. to about −80° C. in step (a).

21. The method of claim 19, wherein the substantially pure diastereomeric compound has a diastereomeric excess (de) of no less than 99.9%.

22. The method of claim 10, wherein tetramethylethylenediamine (TEMED) is added with the organometallic reagent which is n-BuLi.

* * * * *